(12) United States Patent
Klimek

(10) Patent No.: US 12,213,945 B2
(45) Date of Patent: *Feb. 4, 2025

(54) DEVICES AND METHODS FOR NEEDLELESS AND NEEDLED EXTRACTION OF CONTENTS FROM VIALS

(71) Applicant: KLIM-LOC, LLC, Carbondale, CO (US)

(72) Inventor: Robbie Klimek, Carbondale, CO (US)

(73) Assignee: KLIM-LOC, LLC, Carbondale, CO (US)

( * ) Notice: Subject to any disclaimer, the term of this patent is extended or adjusted under 35 U.S.C. 154(b) by 940 days.

This patent is subject to a terminal disclaimer.

(21) Appl. No.: 17/317,455

(22) Filed: May 11, 2021

(65) Prior Publication Data

US 2022/0117846 A1    Apr. 21, 2022

Related U.S. Application Data

(63) Continuation of application No. 17/111,880, filed on Dec. 4, 2020, now Pat. No. 11,007,120.

(Continued)

(51) Int. Cl.
*A61J 1/20* (2006.01)
*A61J 1/14* (2023.01)

(52) U.S. Cl.
CPC .......... *A61J 1/2096* (2013.01); *A61J 1/1412* (2013.01); *A61J 1/2027* (2015.05); *A61J 1/2037* (2015.05); *A61J 1/2044* (2015.05)

(58) Field of Classification Search
CPC ........ A61J 1/412; A61J 1/2037; A61J 1/2027; A61J 1/2044
See application file for complete search history.

(56) References Cited

U.S. PATENT DOCUMENTS 4,493,348 A    1/1985  Lemmons
4,662,878 A    5/1987  Lindmayer
(Continued)

FOREIGN PATENT DOCUMENTS

EP    2804645       4/2017
JP    2005-102782   4/2005
(Continued)

OTHER PUBLICATIONS

Notice of Allowance for U.S. Appl. No. 16/744,927, date4d Jan. 20, 2023 8 pages.

(Continued)

*Primary Examiner* — Leslie R Deak
(74) *Attorney, Agent, or Firm* — Sheridan Ross P.C.

(57) ABSTRACT

A cap assembly includes an access member configured for attachment to a reservoir. The access member includes a first port that enables needleless extraction of contents from the reservoir, and at least one second port that enables needled extraction of the contents from the reservoir. The cap assembly further includes a valve member positioned in or configured to be positioned in the access member to i) enable needleless extraction of the contents of the reservoir through the first port when the first port is attached to a needless extraction device, ii) enable needled extraction of the contents through the at least one second port, and iii) seal the contents of the reservoir at the first port and at the at least one second port prior to and subsequent to the needleless or needled extraction.

20 Claims, 17 Drawing Sheets

Related U.S. Application Data

(60) Provisional application No. 63/091,986, filed on Oct. 15, 2020.

(56) References Cited

U.S. PATENT DOCUMENTS

| | | | |
|---|---|---|---|
| 5,036,992 | A | 8/1991 | Mouchawar et al. |
| 5,509,433 | A | 4/1996 | Paradis |
| 5,569,191 | A | 10/1996 | Meyer |
| 5,573,525 | A | 11/1996 | Watson et al. |
| 5,620,434 | A | 4/1997 | Brony |
| 5,730,418 | A | 3/1998 | Feith et al. |
| 5,833,213 | A | 11/1998 | Ryan |
| 5,971,181 | A | 10/1999 | Niedospial, Jr. et al. |
| 6,056,135 | A | 5/2000 | Widman |
| 6,168,037 | B1 | 1/2001 | Crimard |
| 6,568,439 | B1 | 5/2003 | Se et al. |
| 6,626,309 | B1 | 9/2003 | Jansen et al. |
| 6,635,043 | B2 | 10/2003 | Daubert et al. |
| 6,692,478 | B1 | 2/2004 | Paradis |
| 6,752,965 | B2 | 6/2004 | Levy |
| 7,905,873 | B2 | 3/2011 | Rondeau et al. |
| 10,555,871 | B2 | 2/2020 | Klimek |
| 11,007,120 | B1 * | 5/2021 | Klimek ............ A61J 1/1412 |
| 2002/0115980 | A1 | 8/2002 | Niedospial, Jr. et al. |
| 2004/0186457 | A1 | 9/2004 | Truitt et al. |
| 2005/0159724 | A1 | 7/2005 | Enerson |
| 2006/0249476 | A1 | 11/2006 | Albers et al. |
| 2008/0009822 | A1 | 1/2008 | Enerson |
| 2010/0241088 | A1 | 9/2010 | Ranalletta et al. |
| 2012/0104054 | A1 | 5/2012 | Terwilliger |
| 2012/0265163 | A1 | 10/2012 | Cheng |
| 2017/0138517 | A1 | 5/2017 | Arnold |
| 2017/0314701 | A1 | 11/2017 | Vulkan |
| 2018/0161243 | A1 | 6/2018 | Ariagno et al. |
| 2018/0168929 | A1 | 6/2018 | Stone |
| 2020/0146935 | A1 | 5/2020 | Klimek |
| 2020/0276085 | A1 | 9/2020 | Linkner et al. |

FOREIGN PATENT DOCUMENTS

| | | |
|---|---|---|
| WO | WO 94/03373 | 2/1994 |
| WO | WO 2013/096911 | 6/2013 |
| WO | WO 2018/213524 | 11/2018 |

OTHER PUBLICATIONS

"Drug Reconstitution: Market Needs and Technical Challenges," Controlled Environments, 2011, 5 pages [retrieved online from: www.cemag.us/article/drug-reconstitution-market-needs-and-technical-challenges?page=0,1].

"Needleless Transfer Device," West Pharmaceutical Services, Inc., 2010, 1 page [retrieved online from: www.westpharma.com/SiteCollectionDocuments/Recon/ntd instruction sheet.pdf].

"Oncology Preparation and Delivery System," Victus, 2010, 2 pages [retrieved online from: www.victus.com/products/connector-biosecurity/medical-connector-biosecurity.html].

International Search Report and Written Opinion for International (PCT) Patent Application No. PCT/US2018/033085, dated Jul. 31, 2018 12 pages.

International Preliminary Report on Patentability for International (PCT) Patent Application No. PCT/US2018/033085, dated Nov. 28, 2019 7 pages.

Official Action for U.S. Appl. No. 16/522,172, dated Sep. 19, 2019 16 pages.

Notice of Allowance for U.S. Appl. No. 16/522,172, dated Nov. 15, 2019 8 pages.

Official Action for U.S. Appl. No. 17/111,880, dated Feb. 1, 2021 9 pages.

Extended Search Report for European Patent Application No. 20216848.0, dated Jun. 16, 2021 8 pages.

Official Action for U.S. Appl. No. 16/744,927, dated Aug. 23, 2022 9 pages.

International Search Report and Written Opinion for International (PCT) Patent Application No. PCT/US2021/032399, dated Jun. 24, 2021 8 pages.

Notice of Allowance for U.S. Appl. No. 17/111,880, dated Mar. 16, 2021 5 pages.

International Preliminary Report on Patentability for International (PCT) Patent Application No. PCT/US2021/032399, dated Apr. 27, 2023 7 pages.

Official Action for European Patent Application No. 20216848.0, dated May 24, 2024 6 pages.

Official Action for U.S. Appl. No. 18/322,381, dated Jul. 1, 2024 5 pages.

* cited by examiner

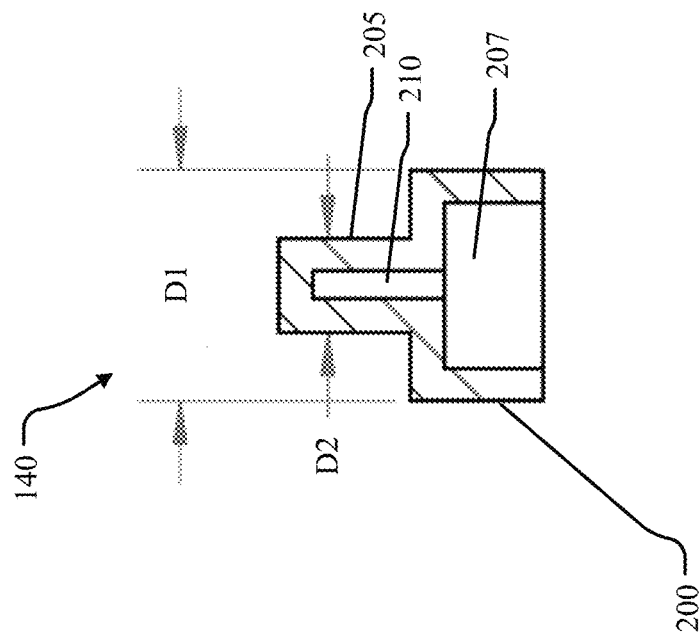
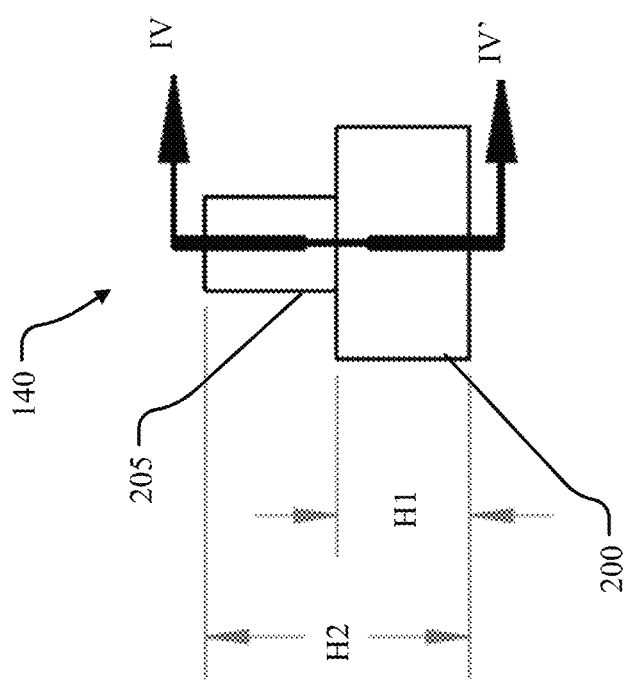
Fig. 4B
Fig. 4A

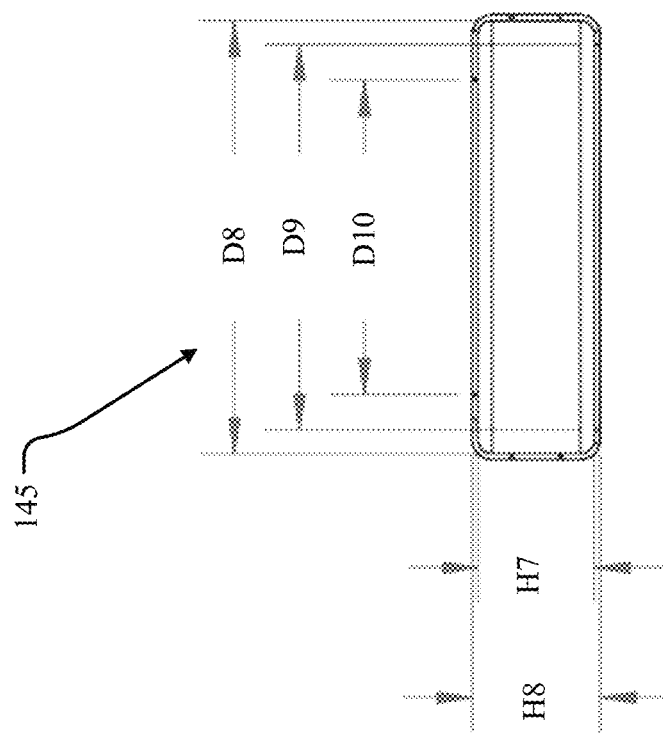
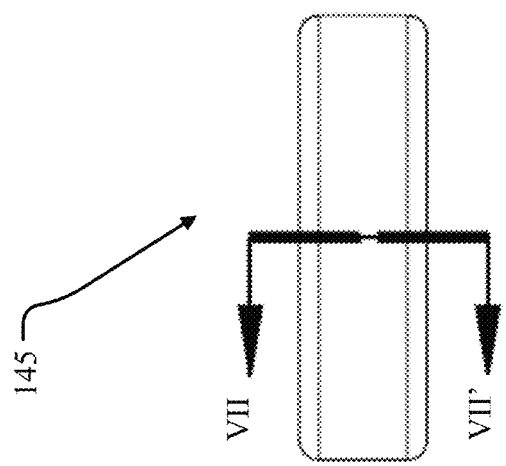
Fig. 7B
Fig. 7A

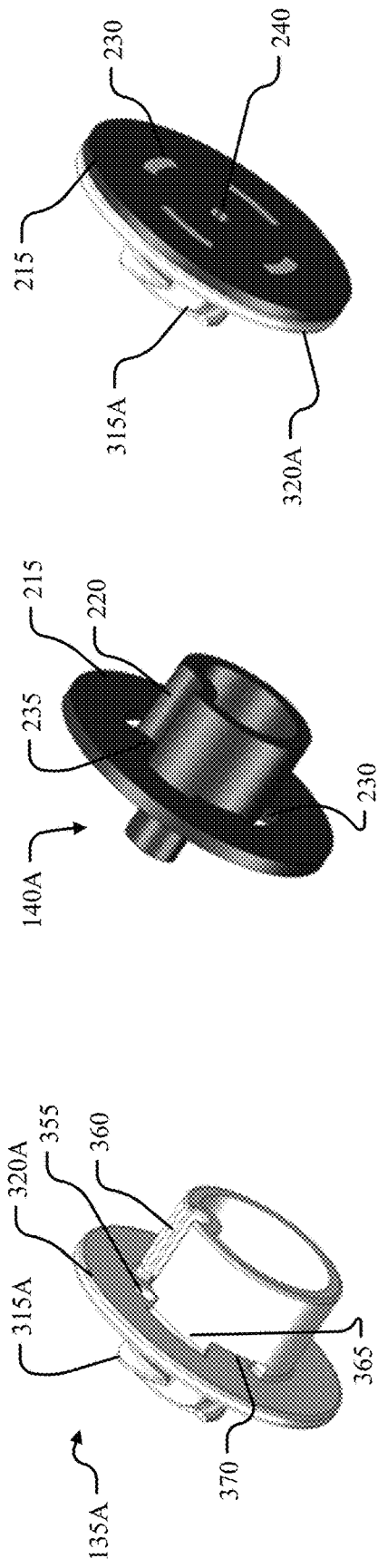
Fig. 14A
Fig. 14B
Fig. 14C
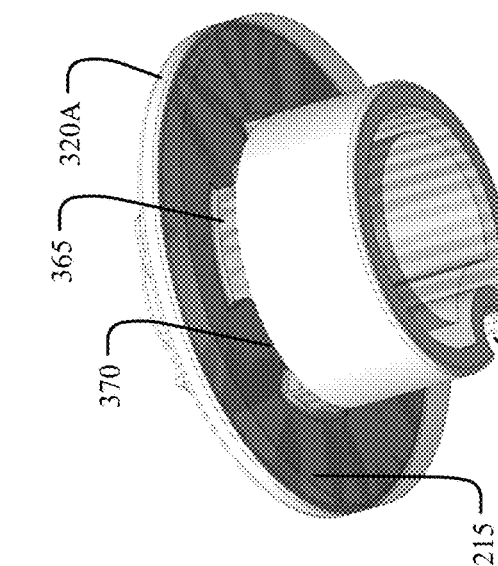
Fig. 14F
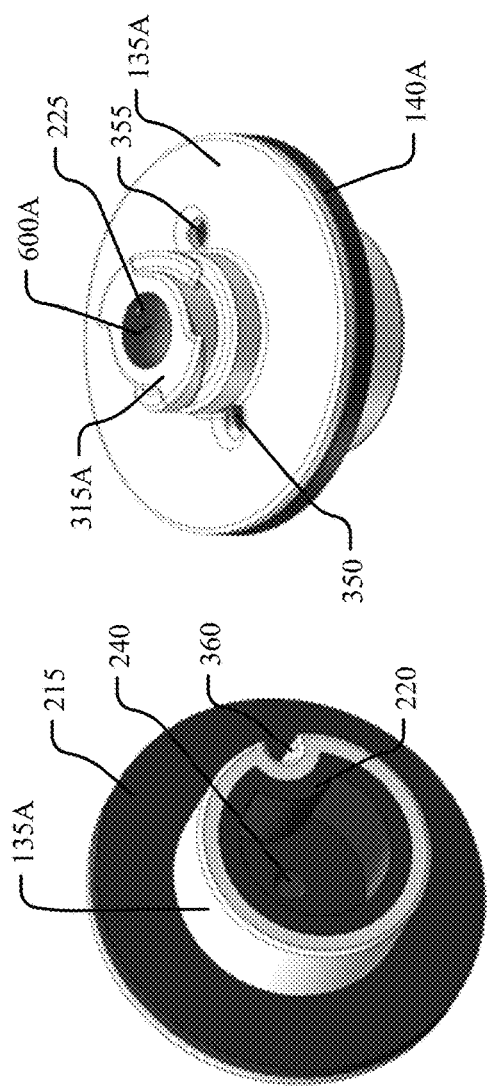
Fig. 14E
Fig. 14D

US 12,213,945 B2

DEVICES AND METHODS FOR NEEDLELESS AND NEEDLED EXTRACTION OF CONTENTS FROM VIALS

CROSS REFERENCE TO RELATED APPLICATIONS

This application is a continuation application of U.S. patent application Ser. No. 17/111,880, filed on Dec. 4, 2020, which claims the benefit of U.S. Provisional Patent Application No. 63/091,986, filed on Oct. 15, 2020, the entire contents of each of which are hereby incorporated by reference.

FIELD

Example embodiments generally relate to devices and/or methods for needleless extraction and/or administration of contents from/to medical reservoirs or vials.

BACKGROUND

In the medical field, liquid is drawn from a vial or other container using a syringe and needle assembly where the needle is manually affixed the syringe and plunged into a penetrable cap of a vial to allow for extraction of the liquid from the vial into the syringe. Following extraction, the syringe/needle assembly may be administered to a patient either directly (e.g., where the needle penetrates the skin of the patient) or intravenously by plunging the needle into some type of chamber on a drip. However, the assembly of the syringe/needle is time consuming, and the extraction/administration process is subject to risks associated with handling unprotected needles (e.g., unintentional needle punctures to people or surrounding objects).

BRIEF DESCRIPTION OF THE DRAWINGS

FIG. 4A illustrates side view of a valve member of the vial assembly in FIG. 1 according to at least one example embodiment;

FIG. 4B illustrates a cross-sectional view of the valve member in FIG. 4A along the line IV-IV' according to at least one example embodiment;

FIG. 7A illustrates a side view of a housing of the vial assembly in FIG. 1 according to at least one example embodiment;

FIG. 7B illustrates a cross-section view of the housing in FIG. 7A along the line VII-VII' according to at least one example embodiment;

FIG. 14A illustrates a bottom perspective view of the access member from FIGS. 11-13 according to at least one example embodiment;

FIG. 14B illustrates a bottom perspective view of the valve member from FIGS. 11-13 according to at least one example embodiment;

FIG. 14C illustrates a bottom perspective view of the assembled access member and valve member from FIGS. 11-13 according to at least one example embodiment;

FIG. 14D illustrates a bottom perspective view of the assembled access member and valve member from FIGS. 11-13 according to at least one example embodiment;

FIG. 14E illustrates a top perspective view of the assembled access member and valve member from FIGS. 11-13 according to at least one example embodiment;

FIG. 14F illustrates a see-through bottom perspective view of the assembled access member and valve member from FIGS. 11-13 according to at least one example embodiment;

DETAILED DESCRIPTION

Figure 1:
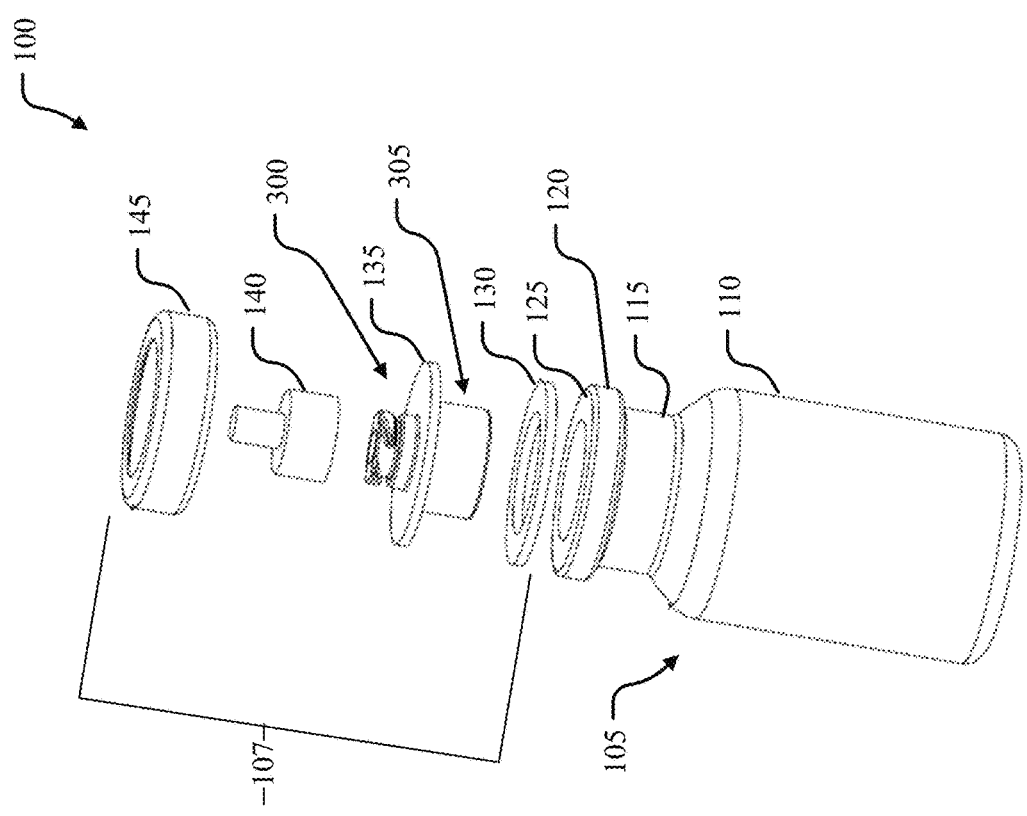
FIG. 1 illustrates an exploded view of a vial assembly according to at least one example embodiment.

Example embodiments include a vial assembly including a vial and a cap assembly that can eliminate the need for using a needle for both the extraction and administration of contents from the vial. The cap assembly includes a valve, a seal or sealing member, an access member, and a hollow housing. The valve and the sealing member may be comprised of a flexible sealing material, such as silicone. The access member may be comprised of a polymer or other plastic-type material and serves as an access port between the valve and the vial. The hollow housing may be comprised of aluminum (e.g., as an aluminum crimp) or other bendable metal that fastens the valve, the seal, and the access member to the vial.

The valve may be a hollow, unitary member that includes two integrated cylindrical portions (top and bottom) that appear concentric from a top view. The valve includes a slit in a top surface that allows liquid to flow through the valve and into the syringe. The valve may be comprised of silicone or another flexible material, such as rubber.

The access member includes a first (top) section and a second (bottom) section. Both sections may be substantially cylindrical from a top view. The first section includes a connection portion that protrudes from a top of the cap assembly and allows for connection to a syringe. For example, the connection portion may include a male thread engagement for connection to a corresponding female thread engagement on the syringe. The connection portion defines a cavity which, when assembled, fits the top portion of the valve so that the valve slit is visible on a surface of the valve that faces away from the vial. The second section also defines the cavity so that, when assembled, the second section fits the bottom portion of the valve. The second section includes an opening to allow for access to the liquid in the vial. The first section and the second section of the access member may be separable from one another at a separation point to allow for installation of the valve into the cavities of the first and second sections. After installation of the valve, the first and second sections may be bonded together by, for example, an adhesive (e.g., glue, an ultraviolet (UV) curable adhesive, a heat curable adhesive, etc.).

The seal or sealing member seals a space between the access member and the vial. The seal may comprise silicone or any other material capable of creating an airtight seal. The seal may be an O-ring seal. Although the seal is shown as being separate from the access member and the vial, it should be understood that the seal may be integrated with/adhered to at least one of the vial and the access member if desired.

The hollow housing may be comprised of a sheet metal, such as aluminum or other suitable material. Although the housing is shown in a crimped state with ends at each opening being bent over, it should be understood that the housing's initial state can be a cylindrical piece of sheet metal that fits over a top of the cap assembly and vial before being crimped on both ends to attach (e.g., permanently attach) the cap assembly to the vial.

The valve may be insertable into the access member so as to be housed within the access member so that the opening in the bottom section of the access member is aligned with the hollow portion of the valve to allow for extraction of liquid from the vial. For extraction, a user attaches a syringe to the male thread engagement of the access member that protrudes from the cap assembly. Here, the syringe has a corresponding female threaded engagement on an inner surface of one end of the syringe that surrounds a hollow protrusion that leads to a plunger section. The hollow protrusion and the female threaded engagement are arranged such that, when the syringe is screwed onto the cap assembly, the hollow protrusion pushes (or compresses) the valve toward the liquid in the vial, which causes the slit in the valve to expand and allow the liquid to flow from the vial through the opening in the access member, the valve, and the hollow protrusion and into the plunger section of the syringe upon pulling on the plunger of the syringe. In one example, the hollow protrusion extends beyond the female threaded engagement so that the protrusion makes the initial contact with the valve. Here, the valve is flexible enough so that the user can push the valve down with protrusion and simultaneously screw the syringe to the cap assembly.

An example syringe may include the hollow protrusion, the female thread on an inner surface and the plunger section.

For needleless administration of the fluid in the syringe, an intravenous (IV) line or drip can have a port that employs the same or similar concepts as those described above with respect to the cap assembly. For example, a drip may have an access port that utilizes the same technology as the valve, the access member, the seal and the housing. Alternatively, the drip (or whatever device is intended to receive the now extracted liquid) may employ an assembly that has the same or similar technology as the valve and the access member, but have a different means of sealing/securing the access member/valve to the drip.

In view of the above, it should be appreciated that example embodiments mitigate (or alternatively, eliminate) the disadvantages and risks of conventional devices that require assembly of a needle to a syringe for both extraction and administration of medicine from a vial. For example, the cap assembly according to example embodiments reduces the time required to assemble a device that can extract liquid from a vial since a needle does not have to be affixed to a separate syringe. Example embodiments also reduce (or alternatively eliminate) the risks associated with using a needle/syringe combination to extract and administer medicine to a patient.

FIG. 1 illustrates an exploded view of a vial assembly 100 according to at least one example embodiment.

As shown in FIG. 1, the vial assembly 100 includes a vial (or reservoir) 105 for holding contents (e.g., liquid contents) and a cap assembly 107 that can eliminate the need for using a needle for both the extraction and administration of contents from the vial 105. The vial 105 includes a body portion 110, a neck portion 115, and a rim portion 120 having a planar upper surface 125.

The cap assembly 107 includes a seal or sealing member 130, an access member 135, a valve or valve member 140, and a housing 145. The valve 140 and the sealing member 130 may be comprised of a flexible sealing material, such as silicone. The access member 135 may include sections or portions 300 and 305 and be comprised of a polymer or other plastic-type material and serves as an access port between the valve 140 and the vial 105. The hollow housing 145 may be comprised of aluminum (e.g., as an aluminum crimp) or other bendable metal that is capable of being crimped. The details of each element in FIG. 1 are described in more detail below with reference to FIGS. 2-10.

Figure 2:
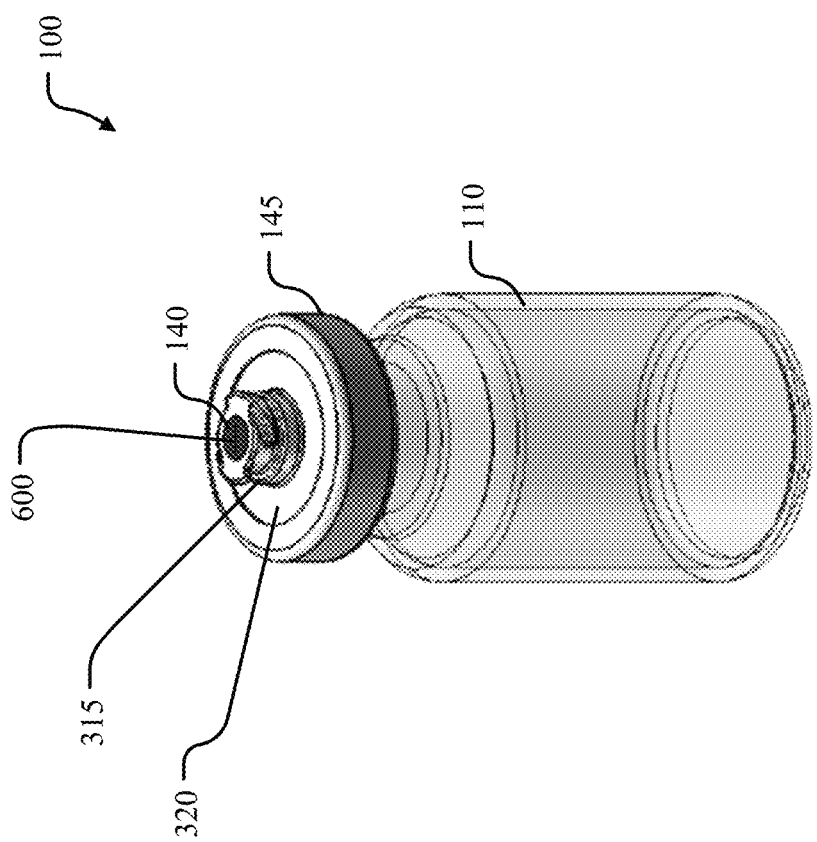
FIG. 2 illustrates an assembled perspective view of the vial assembly of FIG. 1 according to at least one example embodiment.
Figure 3A:
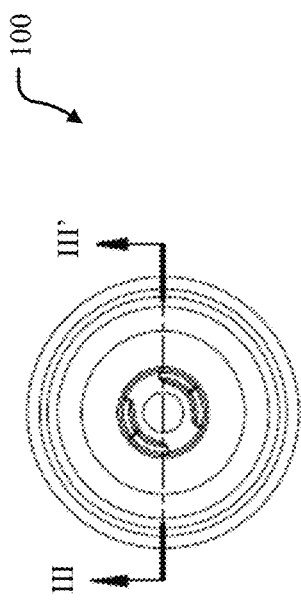
FIG. 3A illustrates an assembled top view of the vial assembly in FIG. 1 according to at least one example embodiment.
Figure 3B:
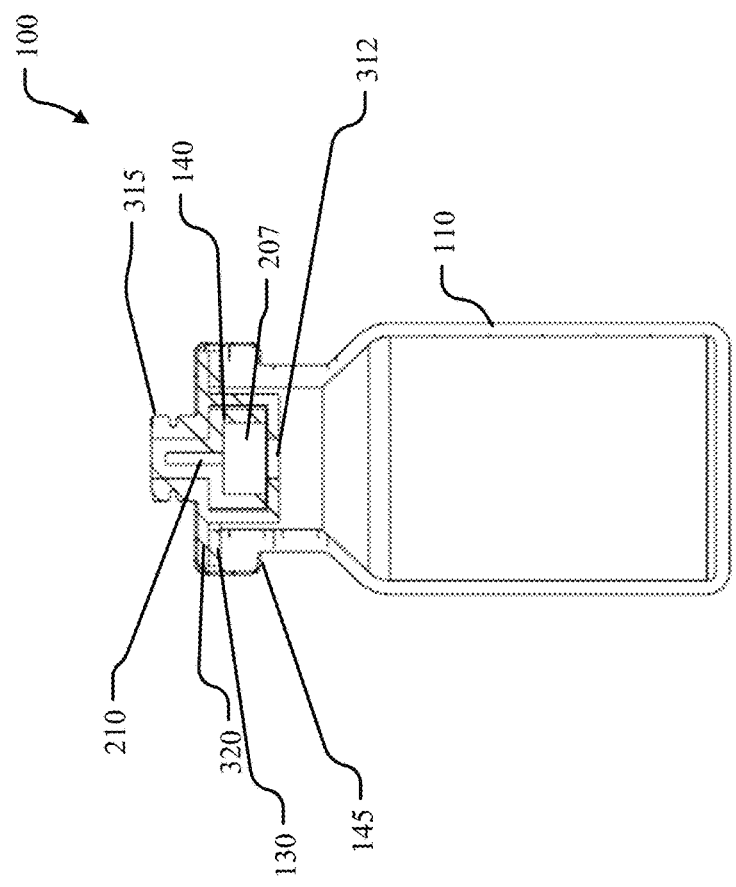
FIG. 3B illustrates a cross-sectional view of the vial assembly in FIG. 3A along the line according to at least one example embodiment.
Figures 5A, 5B:
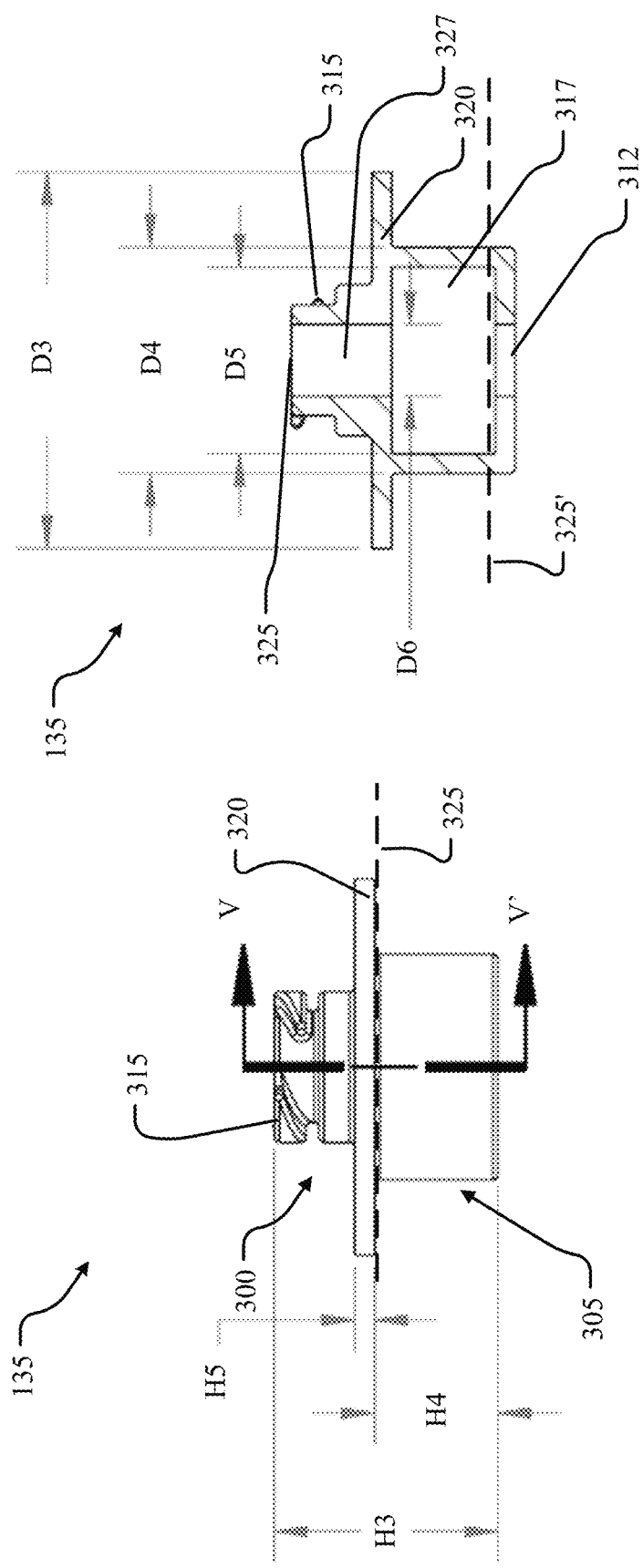
FIG. 5A illustrates a side view of an access member of the vial assembly in FIG. 1 according to at least one example embodiment.
FIG. 5B illustrates a cross-sectional view of the access member in FIG. 5A along the line V-V' according to at least one example embodiment.
Figures 6A, 6B:
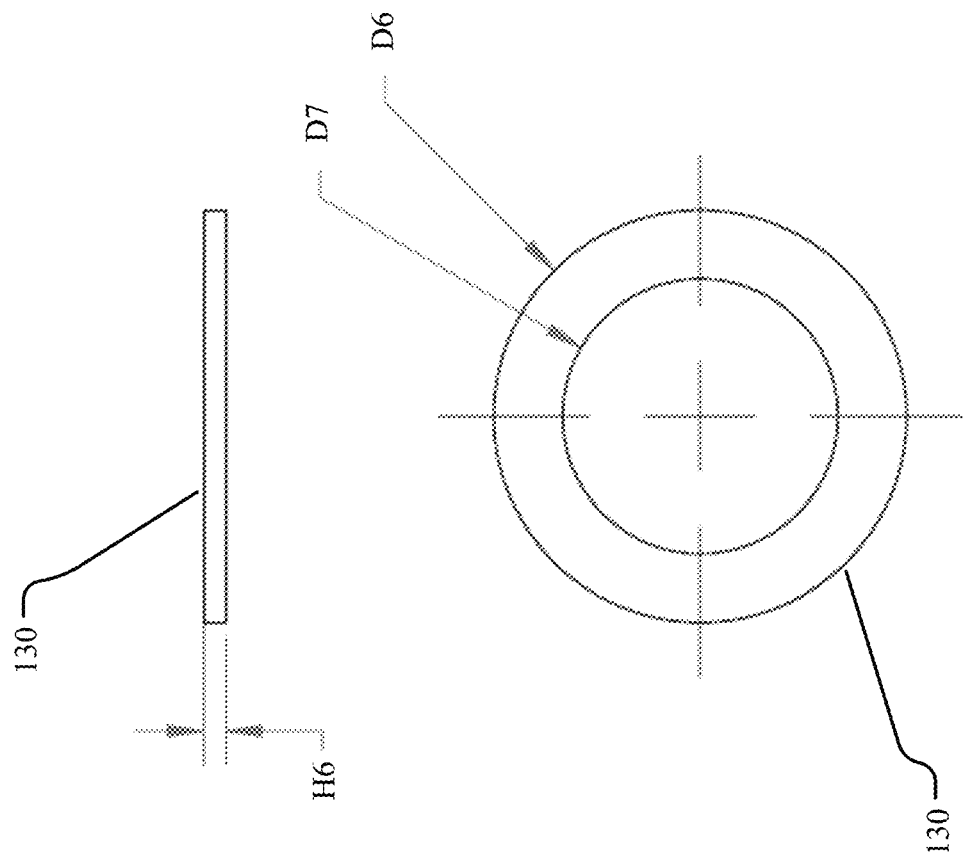
FIG. 6A illustrates a side view of a sealing member of the vial assembly in FIG. 1 according to at least one example embodiment.
FIG. 6B illustrates a top view of the sealing member in FIG. 6A according to at least one example embodiment.

FIG. 2 illustrates an assembled perspective view of the vial assembly 100 of FIG. 1 according to at least one example embodiment. FIG. 3A illustrates an assembled top view of the vial assembly 100 in FIGS. 1 and 2 according to at least one example embodiment. FIG. 3B illustrates a cross-sectional view of the vial assembly 100 in FIG. 3A along the line according to at least one example embodiment. FIG. 4A illustrates side view of a valve 140 of the vial assembly 100 in FIG. 1 according to at least one example embodiment. FIG. 4B illustrates a cross-sectional view of the valve 140 in FIG. 4A along the line IV-IV' according to at least one example embodiment. FIG. 5A illustrates a side view of an access member 135 of the vial assembly 100 in FIG. 1 according to at least one example embodiment. FIG. 5B illustrates a cross-sectional view of the access member 135 in FIG. 5A along the line V-V' according to at least one example embodiment. FIG. 6A illustrates a side view of a sealing member 130 of the vial assembly 100 in FIG. 1 according to at least one example embodiment. FIG. 6B illustrates a top view of the sealing member 130 in FIG. 6A according to at least one example embodiment. FIG. 7A illustrates a side view of a housing 145 of the vial assembly in FIG. 1 according to at least one example embodiment. FIG. 7B illustrates a cross-section view of the housing 145 in FIG. 7A along the line VII-VII' according to at least one example embodiment.

As shown in FIG. 2, by way of crimping the housing 145, the remainder of the cap assembly 107 is fixable to the vial 105. For example, the housing 145 slides over the valve 140, the sealing member 130, and the access member 135, and the rim portion 120 before being crimped around the access member 135 and the rim portion 120 to fasten the cap assembly 107 to the vial 105.

With reference to FIGS. 1-7B, the cap assembly 107 may include the access member 135 including a first section 300 and a second section 305 (see FIG. 1 and FIGS. 5A and 5B). The first section 300 includes a connection portion (or first port) 315 that is attachable to an extraction device (e.g., a syringe 800 as in FIGS. 8A-9) that extracts (or inserts) contents of the reservoir 105. As shown in FIGS. 3B, 5A and 5B, the connection portion 315 includes a first opening 325, and the second section 305 includes a second opening 312 in fluid communication with the contents of the reservoir 105 when the access member 135 is secured to the reservoir 105. As also shown in FIGS. 5A and 5B, the connection portion 315 may protrude from the access member 135 and include a male connector, such as a male connector with an outer thread for a screw connection to a corresponding female connector with an inner thread (see FIGS. 8A and 8B).

As shown in FIGS. 1-3B, the valve member 140 is insertable into the access member so as to be housed within the access member so that the opening 312 in the second section 305 of the access member 135 is aligned with the hollow portions 207/210 of the valve 140 to allow for extraction of contents from the vial 105. As shown in FIG. 2, the valve member 140 may include a top portion with a slit 600, which is located in the first opening 325 of the connection portion 315 when the cap assembly 107 is fixed to the vial 105. According to at least one example embodiment, the valve member 140 is comprised of a flexible material, such as silicone, so that the valve member 140 is compressible relative to the first opening 325. Here, it should be appreciated that the slit 600, in an uncompressed state of the valve member 140, is closed and seals the contents of the reservoir 105 at the first opening 325 when the connection portion 315 is not attached to the extraction device. Additionally, the slit 600, in a compressed state of the valve member 140, opens and provides the access to the contents of the reservoir 105 when the connection portion 315 is attached the extraction device (e.g., syringe 800 in FIGS. 8A and 8B). Upon attachment of the connection portion 315 to the extraction device, contents of the reservoir 105 are ready to be extracted. In other words, the valve member 140 is insertable into the access member 135 so as to be housed in the access member 135 and in fluid communication with the first opening 325 and the second opening 315 and such that the valve member 140 i) seals the contents of the reservoir 105 at the first opening 325 when the connection portion 315 is not attached the extraction device (e.g., syringe 800 in FIG. 9), and ii) provides access to the contents of the reservoir 105 through the first opening 325 when the connection portion 315 is attached to the extraction device.

As shown in FIGS. 4A and 4B, the valve member 140 may have a first section 200 and a second section 205. The first section 200 and the second section 205 are substantially cylindrical shaped. The first section 200 includes a first hollow portion 207 and the second section 205 includes a second hollow portion 210. As shown in FIGS. 3A and 3B, the hollow portions 207/210 are in fluid communication with the reservoir 105 through the opening 312 in the access member 135. In addition, the hollow portion 210 is fluid communication with the slit 600 in FIG. 2 to allow for extraction of the contents from the reservoir 105. The first section 200 may have a height H1 of about 0.200 in, and a diameter D1 of about 0.350 in. The first and second sections 200 and 205 may have a total height H2 of about 0.400 in. The second section 205 may have a diameter D2 of about 0.143 in.

As shown in FIGS. 5A and 5B, the access member 135 includes the first section 300 and the second section 305. In order to allow the valve member 140 to be inserted into the access member 135 (as shown in FIGS. 2 and 3B), the access member 135 may be physically cut into the first section 300 and the second section 305, for example, along the line 325. Alternatively, sections 300 and 305 are manufactured as separate pieces. In any event, after the valve member 140 is inserted into the one of the sections 300/305, the sections 300 and 305 are adhered to one another, for example, by ultraviolet (UV) curing, heat curing, or other suitable adhesive technique. In other words, the first section 300 and the second section 305 are detachably connected. Thus, according to at least one example embodiment, the sections 300 and 305 comprise a UV or heat curable material. Although FIG. 5A shows that the sections 300 and 305 are separated along the line 325, it should be appreciated that other separation locations may be used according to design and/or manufacturing preferences. For example, FIG. 5B shows another example separation location along the line 325'. The first section 300 may include a planar portion 320 that is designed to rest on the sealing member 130 and be supported by the rim portion 125 of the vial 105. As shown in FIGS. 3B and 5B, the access member 135 includes hollow portions 317 and 327 to accommodate the valve member 140.

As shown in FIGS. 5A and 5B, the access member 135 has a total height H3 of about 0.445 in., the second section 305 has a height H4 of about 0.246 in, and the planar portion 320 has a height H5 of about 0.039 in. In addition, a diameter D3 of the access member 135 is about 0.750 in., a diameter D4 of the second section 305 is about 0.450 in., a diameter D5 of the hollow portion 317 is about 0.371 in, and a diameter D6 of the openings 312 and 325 is about 0.143 in.

As shown in FIGS. 6A and 6B, a height H6 of the sealing member 130 may be about 0.040 in., an outer diameter D6 of the sealing member 130 is about 0.750 in, and an inner diameter D7 of the sealing member 130 is about 0.500 in. With reference to FIGS. 1 and 3B, it should be appreciated that the sealing member 130 seals an interface between the reservoir 105 (e.g., the planar surface 125) and the planar portion 320 of the access member 135. The sealing member 130 may be comprised of a flexible sealing material, such as rubber, silicone, or other suitable sealing material. Although the sealing member 130 is shown as an element separate from the vial 105, it should be understood that the sealing member 130 may also be integrated with the vial 105, for example, via a pre-existing attachment to the planar surface 125 of the rim portion 120.

FIGS. 7A and 7B illustrate additional details of the housing 145. As noted above, the housing 145, secures the access member 135 and the sealing member 130 to the reservoir 105. According to at least one example embodiment, the housing 145 is a bendable and hollow cylinder with openings at each end. To secure the access member 135 and the sealing member 130 to the vial 105, the housing 145 slides over the remainder of the cap assembly 107 and the rim portion 125. Then, both ends of the housing 145 are bent (or crimped) toward a center of the housing 145 to fix the cap assembly 107 to the vial 105. According to at least one example embodiment, the housing is a metal, such as aluminum.

As shown in FIGS. 7A and 7B, a final, assembled, height H7 of the housing 145 may be about 0.211 in., while an initial, pre-assembled, height H8 of the housing 145 may be about 0.231 in. Here, the initial height H8 refers to a height of the housing prior to attachment of the cap assembly 107 to the vial 105, i.e., prior to the ends of the housing 145 being bent toward the center of the housing 145 to secure the access member 135 and the sealing member 130 to the vial as shown in FIG. 2. In addition, the final height H7 refers to a height of the housing 145 after attachment of the cap assembly 107 to the vial 105, i.e., after bending the ends of the housing 145 toward the center to secure the access member 135 and the sealing member 130 to the vial 105 as shown in FIG. 2. An outer diameter D8 of the housing 145 may be about 0.787 in., an intermediate diameter D9 of the housing 145 may be about 0.700 in., and an inner diameter D10 of the housing 145 may be about 0.570 in.

Figures 8A, 8B:
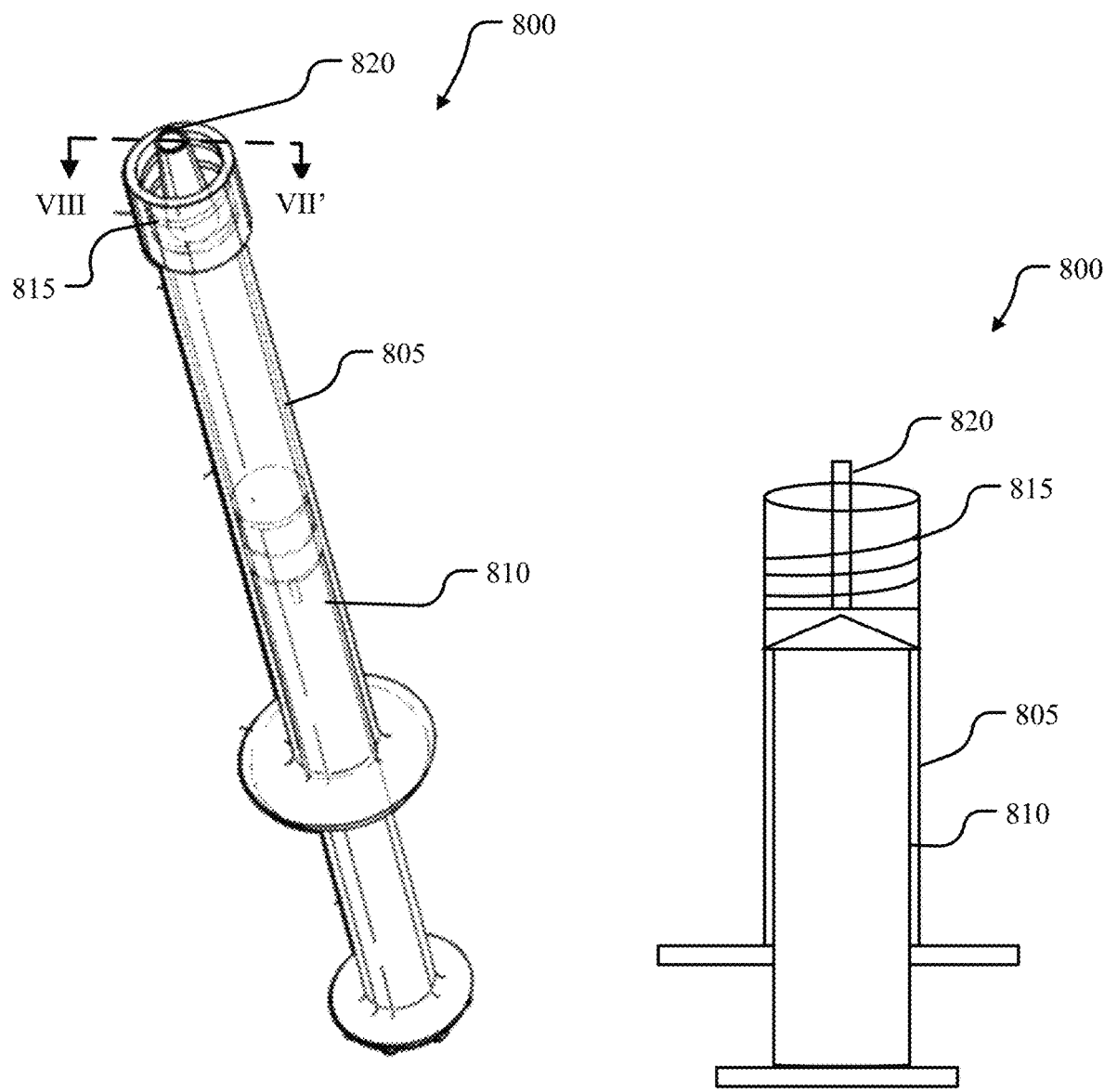
FIG. 8A illustrates a perspective view of a syringe according to at least one example embodiment.
FIG. 8B illustrates a cross-sectional view of the syringe in FIG. 8B along the line VIII-VIII' according to at least one example embodiment.

FIG. 8A illustrates a perspective view of a syringe 800 according to at least one example embodiment. FIG. 8B illustrates a cross-sectional view of the syringe 800 in FIG. 8B along the line VIII-VIII' according to at least one example embodiment.

As shown in FIGS. 8A and 8B, the syringe 800 includes a hollow holding portion 805, a plunger 810, a connection portion 815, and a tip 820. The connection portion 815 may include a female thread for engagement with the male thread of the connection portion 315. The tip 820 may protrude beyond an upper surface of the connection portion 815 in order to allow for the tip 820 to penetrate the connection portion 315 when connecting the syringe 800 to the vial assembly 100, thereby compressing the valve member 140.

Figure 9:
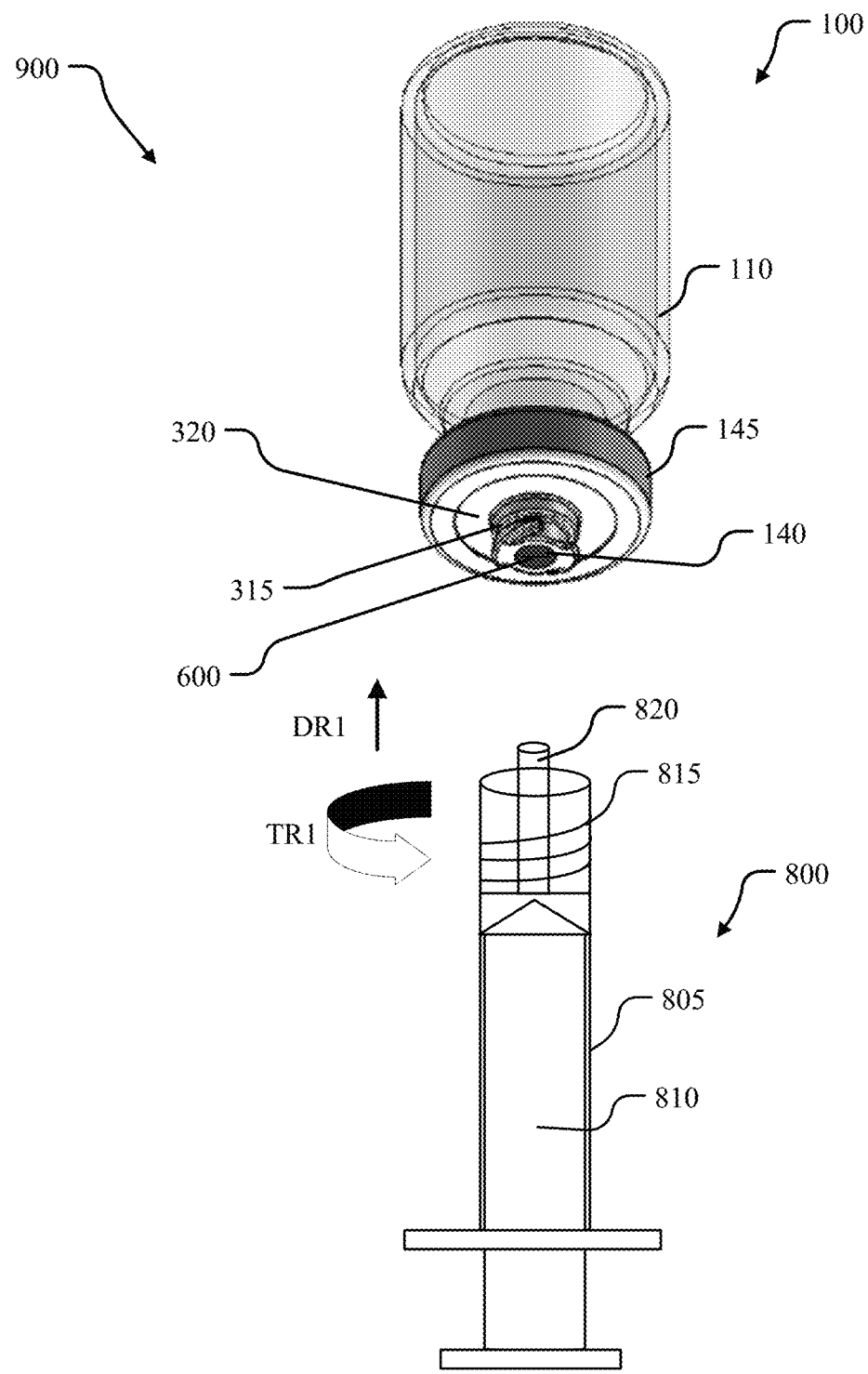
FIG. 9 illustrates a package including the syringe in FIGS. 8A and 8B and the vial assembly of FIGS. 1-7B according to at least one example embodiment.

FIG. 9 illustrates a package 900 including the syringe 800 in FIGS. 8A and 8B and the vial assembly 100 of FIGS. 1-7B according to at least one example embodiment. FIG. 9 illustrates an example of the syringe (or extraction device) 800 being moved in a direction DR1 toward the vial assembly 100 such that the tip 820 penetrates the connection portion 315 to thereby compress the valve member 140 and open the slit 600 to provide access to the contents of the vial 105. As the tip 820 compresses the valve member 140, the syringe 800 may be twisted in the clockwise direction TR1 in order to engage the female thread on the connection portion 815 with the male thread on the connection portion 315. Now, the syringe 800 and the vial assembly 100 are attached to one another in a manner that allows the contents of the vial to be extracted or inserted by, for example, actuation of the plunger 810. In order to release the syringe 800 from the vial assembly 100, the syringe 800 may be twisted in the counter-clockwise direction to disengage the female thread of the connection portion 815 from the male thread of the connection portion 315.

In view of FIGS. 1-9, it should be understood that the valve member 140 is insertable into the access member 135 so as to be housed in the access member 135 and in fluid communication with the first opening 325 and the second opening 315 such that the valve member 140 i) seals the contents of the reservoir 105 at the first opening 325 when the connection portion 315 is not attached the extraction device 800, and ii) provides access to the contents of the reservoir 105 through the first opening 325 when the connection portion 315 is attached to the extraction device 800. Here, it should be appreciated that the slit 600, in an uncompressed state of the valve member 140, seals the contents of the reservoir 105 at the first opening 325 when the connection portion 315 is not attached to the extraction device 800. Additionally, the slit 600, in a compressed state of the valve member 140, provides the access to the contents of the reservoir 105 when the connection portion 315 is attached the extraction device (e.g., syringe 800 in FIG. 9). Upon attachment of the connection portion 315 to the extraction device 800, contents of the reservoir 105 are ready to be extracted.

Figure 10:
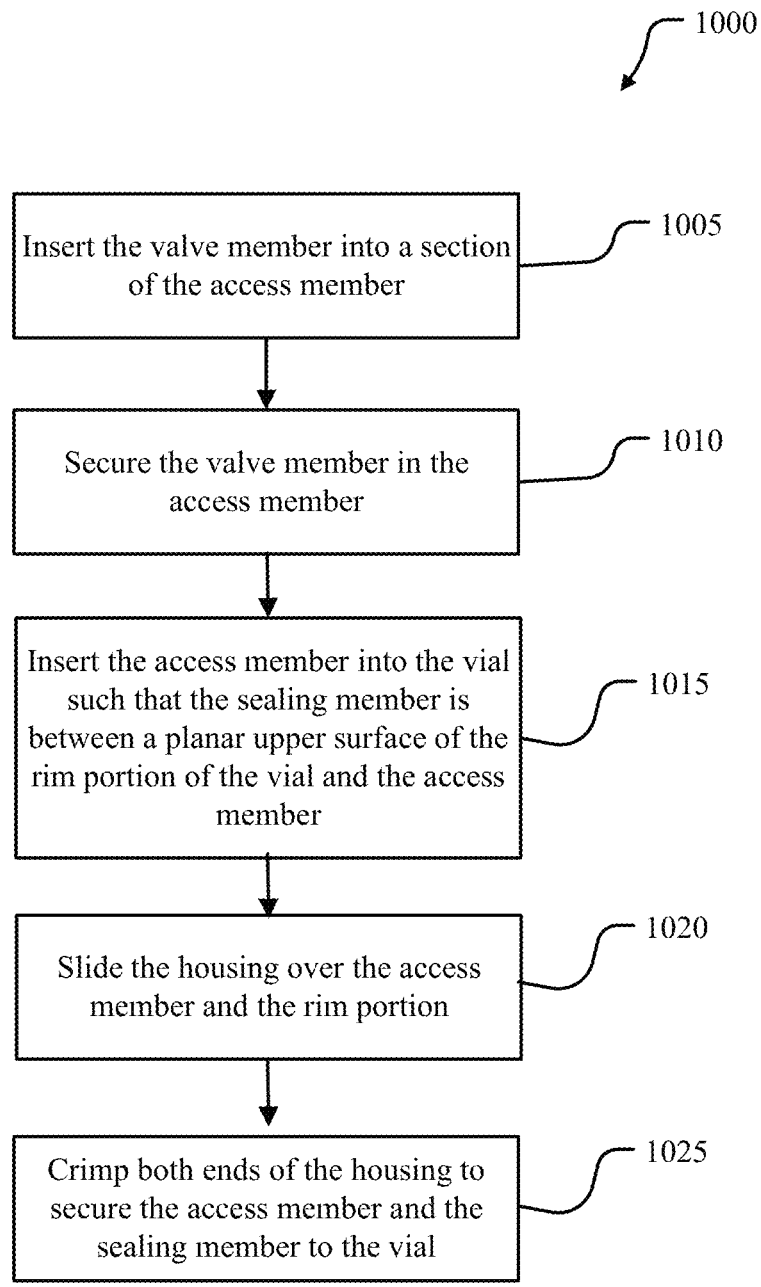
FIG. 10 illustrates a method of manufacturing the vial assembly in FIGS. 1-7B according to at least one example embodiment.

FIG. 10 illustrates a method 1000 of manufacturing the vial assembly 100 in FIGS. 1-7B according to at least one example embodiment.

While a general order for the steps of the method 1000 is shown in FIG. 10, the method 1000 can include more or fewer steps or can arrange the order of the steps differently than those shown in FIG. 10 if desired. Hereinafter, the FIG. 10 shall be explained with reference to the systems, components, assemblies, devices, user interfaces, environments, software, etc. described in conjunction with FIGS. 1-9.

In operation 1005, the method 1000 includes inserting the valve member 140 into a section of the access member 135. As noted above, the access member 135 is split into sections, for example, sections 300/305 to allow for insertion of the valve member 140.

In operation 1010, the method 1000 includes securing the valve member 140 in the access member 135, for example, by adhering section 300 to section 305 using a suitable adherent and/or adhering process.

In operation 1015, the method 1000 includes inserting the access member 135 into the vial 105 (e.g., the neck 115) such that the sealing member 130 is between the planar upper surface 125 of the rim portion 120 and the access member 135 (e.g., a bottom surface of the planar portion 320).

In operation 1020, the method 1000 includes sliding the housing 145 over the access member 135 and the rim portion 120.

In operation 1025, the method 1000 includes crimping (or bending) both ends of the housing 145 to secure the access member 135 and the sealing member 130 to the vial 105. For example, one end of the housing 145 is bent toward a central axis of the vial 105 in order to make contact with an upper surface of the planar portion 320. The other end of the housing is bent toward the central axis of the vial 105 so as to make contact with a bottom surface of the rim portion 120. Now, cap assembly (including the sealing member 130, the access member 135, the valve member 140, and the housing 145 are secured to the vial 105 to complete the vial assembly 100.

FIGS. 11-17 illustrate various views of vial assemblies according to additional example embodiments. FIGS. 11-17 include some of the same elements referenced above in the description of FIGS. 1-10. Accordingly, these elements include the same numbering in FIGS. 11-17 as in FIGS. 1-10 and a description of these elements will not be repeated.

Figure 11:
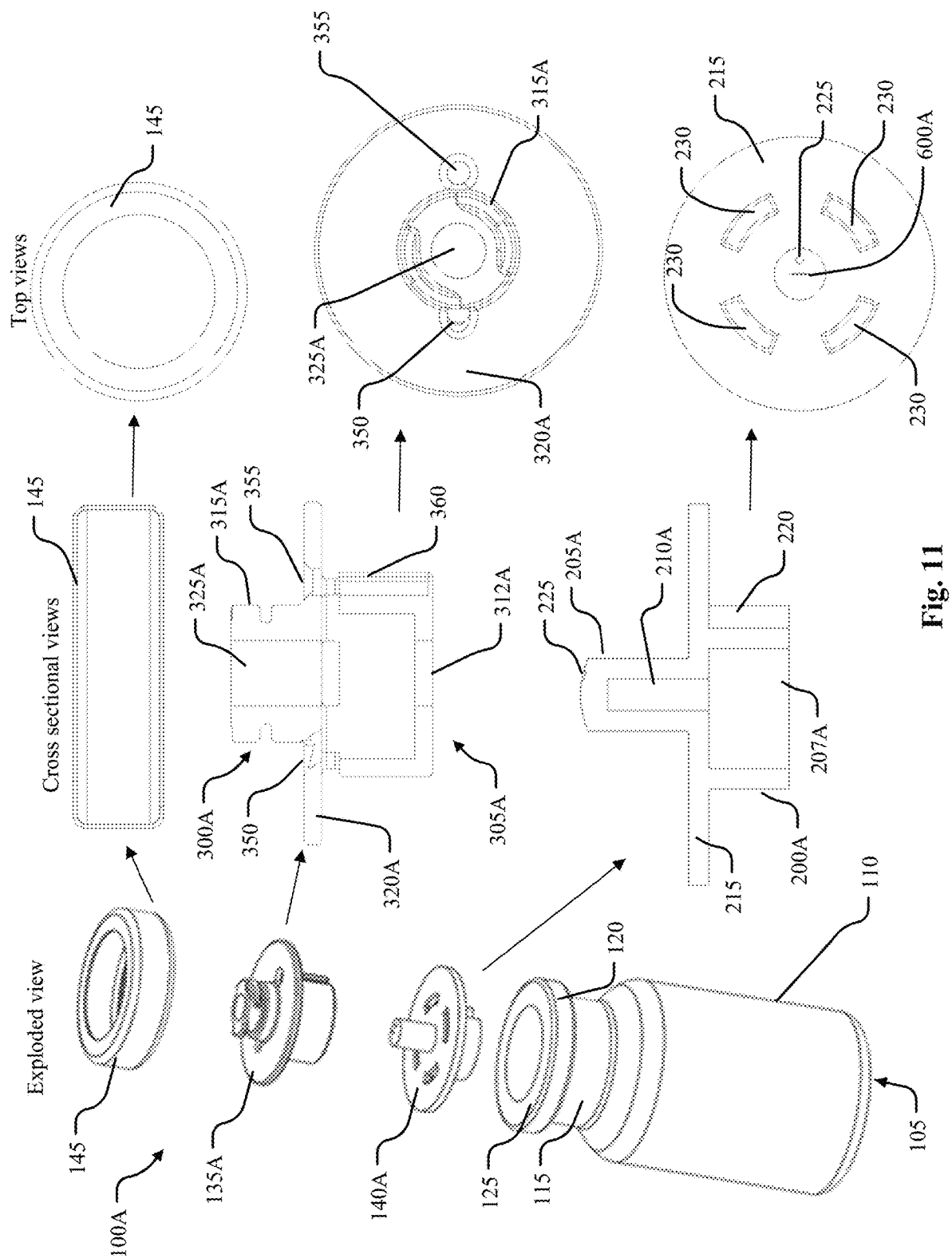
FIG. 11 illustrates an exploded view of a vial assembly according to at least one example embodiment as well as various cross-sectional and top views for certain elements of the vial assembly.

FIG. 11 illustrates an exploded view of a vial assembly 100A according to at least one example embodiment as well as various cross-sectional and top views for certain elements of the vial assembly 100A.

As in FIGS. 1-10, the vial assembly 100A includes a housing 145 and a female luer or access member 135A. Compared to FIGS. 1-10, the valve member and sealing member or septum are integrated with one another as valve member 140A (or integrated valve and sealing member), thereby reducing the number of individual parts compared to FIGS. 1-10. Similar to FIGS. 1-10, the access member 135A and the valve member 140A are fixed to the vial 105 with the housing 145 (e.g., aluminum or other bendable material).

FIG. 11 illustrates an example where the access member 135A includes a first port (or connection portion) 315A that enables needleless extraction as in FIGS. 1-10 through opening 325A and at least one second port that enables needled extraction of the contents from the vial 105. FIG. 11 shows two second ports 350 and 355 that enable needled extraction of contents from the vial 105. The ports 350 and/or 355 may be useful if, for example, the port 315A is damaged or otherwise unusable to extract contents from the vial 105.

As shown, the access member 135A includes a planar portion 320A and a first portion 300A including port 315A that protrudes from a first side of the planar portion 320A. The port 315A is attachable to a needleless extraction device (e.g., device 800 from FIG. 8). For example, as in FIGS. 1-10, the first portion 300A of port 315A includes threading that engages with corresponding threading on a needleless extraction device. The access member 135A includes a second portion 305A that protrudes from a second side of the planar portion 320A opposite the first side. The second portion 305A includes a groove 360.

The ports 350 and 355 comprise respective openings in the planar portion 320A of the access member 135A. As shown, the opening for port 350 may be formed in the planar portion 320A to have angled sidewalls. The angle of the sidewalls may correspond to an angle that guides a needle toward the contents of the vial 105 through opening 312A of the access member 135A. On the other hand, the opening for port 355 may be formed in the planar portion 320A to have substantially straight sidewalls. As shown in FIG. 11, the port 355 is aligned with the groove 360 in the access member 135A. The groove 360 serves as a guide to guide a needle attached to a syringe to the contents of the vial 105. The groove 360 is shown as extending in a direction substantially perpendicular to the planar portion 320A but the groove 360 may also be formed to angle inward or outward away from or toward a central vertical axis of the vial 105.

The access member 135A may be formed of molded plastic or other suitable material. The ports 350 and 355 are shown as being formed on opposite sides of the access member 135A and at a base of port 315A, but example embodiments are not limited thereto and the ports 350 and 355 may be formed at other locations on the planar portion 320A. Although not explicitly shown, it should be appreciated that if the housing 145 extends all the way to the base of the port 315A, then the housing 145 may also include openings aligned with ports 350 and 355.

The valve member 140A includes a first section 200A that protrudes from a planar portion 215, and a second section 205A that protrudes from an opposite side of the planar portion 215. As in FIGS. 1-10, the valve member 140A includes hollow sections 210A and 207A that fit into corresponding hollow sections of the access member 135A. The valve member 140A further includes a groove 220 to match the groove 360 of the access member 135A. When assembled, the groove 220 is at an interior of the access member 135A.

In at least one example embodiment, the valve member 140A is positioned in or configured to be positioned in the access member 135A to i) enable needleless extraction of the contents of the reservoir 105 through the first port 315A when the first port 315A is attached to a needleless extraction device 820, ii) enable needled extraction of the contents through the at least one second port 350 and/or 355, and iii) seal the contents of the reservoir 105 at the first port 315A and at the at least one second port 350 and/or 355 prior to and subsequent to the needleless or needled extraction (e.g., seal the contents at all times other than during extraction). When assembled, small portions of the valve member 140A are exposed by the ports 350 and 355. Thus, as in FIGS. 1-10, the valve member 140A is formed of a material (e.g., silicone) that allows a needle to pass through the material to the contents of the vial 105 while still sealing the contents upon removal of the needle.

Here, it should be appreciated that although FIG. 11 illustrates that the valve member 140A is separate from the access member 135A, it should be appreciated that the valve member 140A may be formed by an over molding process in which a material of the valve member 140A is over molded onto the access member 135A (see FIGS. 14A to 14F for more detail).

As further shown in FIG. 11, the valve member 140A includes a slit 600A, a dimple 225 to further assist with needled extraction through a tip of the valve member 140A if desired, and openings 230 in the planar portion 215. The openings 230 are formed as a result of the over molding process mentioned above in that the access member 135A includes pillars (not depicted in FIG. 11) around which the material of the valve member 140A is formed to create the openings 230. Although four openings 230 are shown, more or fewer openings may be included as desired.

Here, it should be appreciated that FIG. 11 illustrates views for a vial assembly having the same needleless extraction capabilities as described above with reference to FIGS. 1-10 with the addition of three possible "backup" ports that allow for extraction of the contents using a needle: a dimple 225 on the valve member 140A to assist with needle insertion, a straight needle port 355 that guides a needle to the contents in substantially a straight line, and an angled needle port 350 that guides a needle to the contents at an angle. However, it should be appreciated that there may be more or fewer than the three ports for needle extraction. For example, there may be zero dedicated ports for needle extraction similar FIGS. 1-10. In this case, the ports 350 and 355 and the grooves 220 and 360 are omitted (see FIG. 15 for such an example where the dimple 225 would be removed in addition to the ports 350 and 355).

Figure 12:
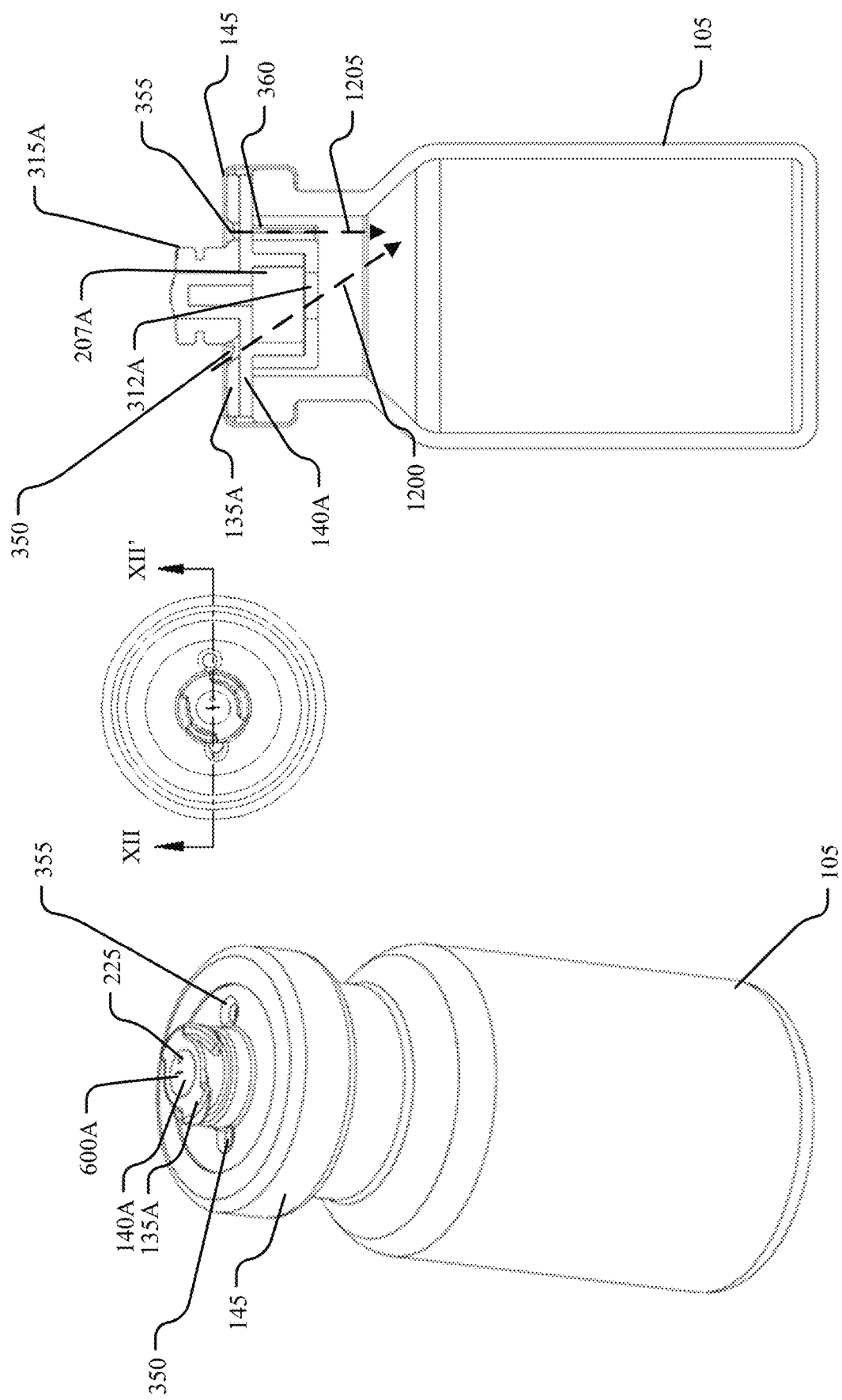
FIG. 12 illustrates various assembled views for the vial assembly of FIG. 11 according to at least one example embodiment.

FIG. 12 illustrates various assembled views for the vial assembly 100A of FIG. 11. In more detail, FIG. 12 illustrates a perspective view, a top view, and a cross-sectional view taken along line XII-XII' of the top view. As shown in FIG. 12, when fully assembled, portions of the valve member 140A are exposed by the ports 315A, 350, and 355 to allow for needleless and needled extraction of contents from the vial 105. As noted above, the port 350 has angled sidewalls to assist with directing a needle along path 1200 to contents of the vial 105. The angle of the sidewalls may be designed such that the needle is guided through opening 312A in the access member 135A. The port 355 is aligned with groove 360 to guide a needle along path 1205 to the contents of the vial 105. As further shown, the housing 145 secures the access member 135A and the valve member 140A to the vial 105 in the same or similar manner as the housing from FIGS. 1-10. In FIG. 12, an outer edge of the planar portion 320A of the access member 135A is sandwiched between the housing 145 and an outer edge of the planar portion 215 of the valve member 140A to effectively seal the contents of the vial 105.

Figure 13:
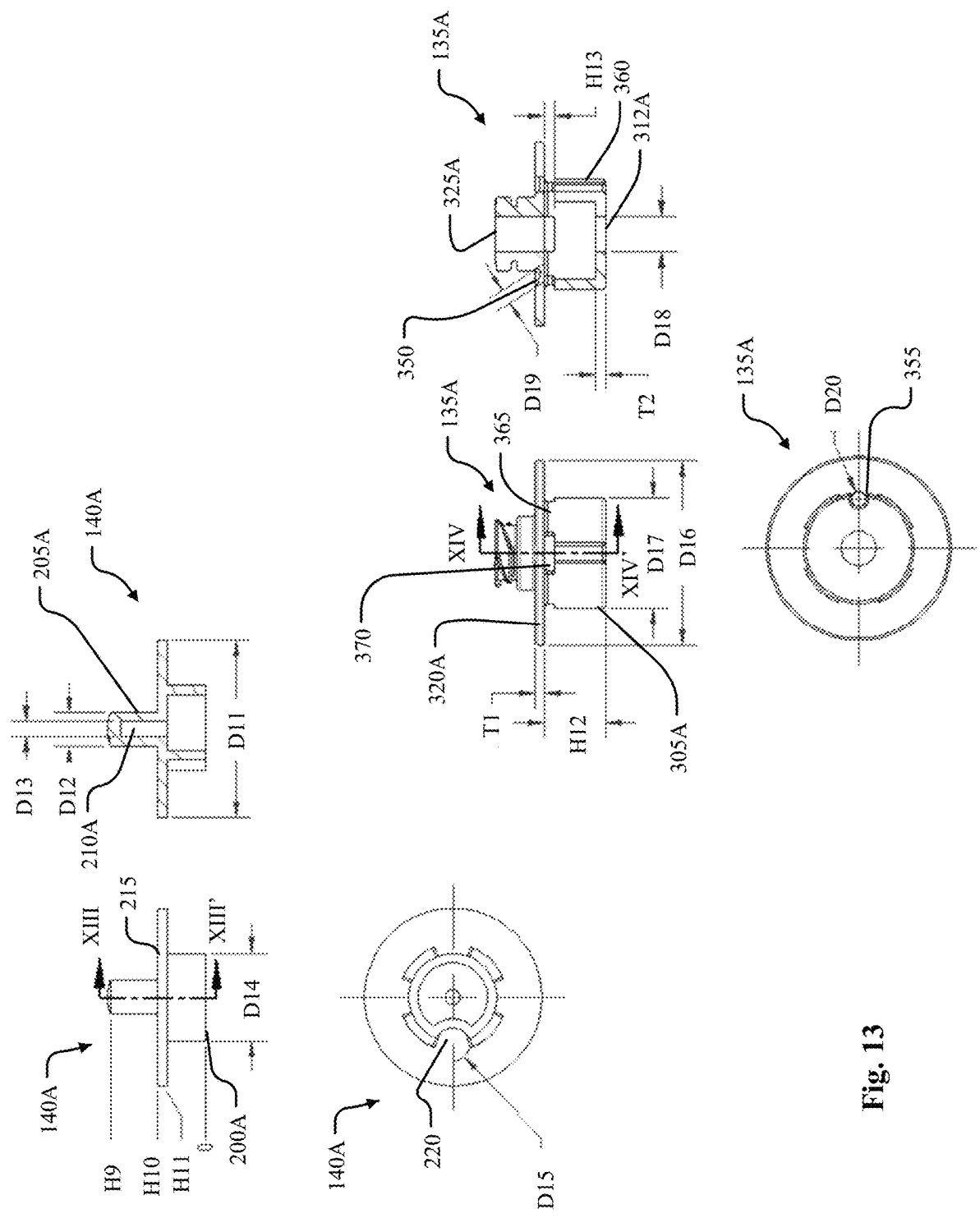
FIG. 13 illustrates example dimensions for the access member and the valve member in FIGS. 11 and 12 according to at least one example embodiment.

FIG. 13 illustrates example dimensions for the access member 135A and the valve member 140A in FIGS. 11 and 12 according to at least one example embodiment. FIG. 13 illustrates a top view, a side view and a cross-sectional view for each of the access member 135A and the valve member 140A. The cross-sectional view for the valve member 140A is taken along line XIII-XIII' while the cross-sectional view for the access member 135A is taken along line XIV-XIV'.

A diameter D11 of planar portion 215 of the valve member 140A may be about 0.750 in. The section 205A has a diameter D12 of about 0.143 in. while the hollow section 210A has a diameter D13 of about 0.063 in. A total height H9 of the valve member 140A is about 0.400 in. A height H10 from a bottom of the valve member 140A to a top of the planar portion 215 is about 0.200 in. while a height H11 from a bottom of the valve member 140A to a bottom of the planar portion 215 is about 0.160. A diameter D14 of the section 200 is about 0.0371 in. As further shown, a diameter D16 of the groove 220 is about 0.070 in.

Turning to the access member 135A, a diameter of the planar portion 320A is about 0.750 in. and a diameter D17 of section 305A is about 0.450 in. A height H12 of the section 305A is about 0.246 in. while a thickness T1 of the planar portion 320A is about 0.039 in. Although not explicitly shown, a total height of the access member 135A may be slightly more than the total height of the valve member 140A in order to accommodate the valve member 140A. Diameters D18 of the openings 312A and 325A are about 0.143 in. while a diameter D19 of the port 350 is about 0.060 in. A diameter D20 of the port 355 may also be about 0.060 in. A thickness T2 of the portion of the access member 135A that creates the opening 312A is about 0.039 in. and a height H13 of a pillar 365 and corresponding opening 370 is about 0.040 in.

Here, it should be appreciated that the dimensions of the housing 145 in FIGS. 11 and 12 are substantially the same as the dimensions of the housing described with reference to FIGS. 1-10.

FIGS. 14A to 14F illustrate various assembled and unassembled views of the access member 135A and the valve member 140A in FIGS. 11-13 according to at least one example embodiment. In more detail, FIG. 14A illustrates a view of the access member 135A, FIG. 14B illustrates a view of the valve member 140A, and FIGS. 14C to 14F illustrate various assembled views for the access member 135A and the valve member 140A (noting that FIG. 14C does not illustrate bottom portions of the access member 135A and the valve member 140A for the sake of explanation).

FIG. 14A illustrates a bottom perspective view of the access member 135A to show that the access member 135A includes pillars 365 and openings 370. The pillars 365 and openings 370 may facilitate an over molding process where a material of the valve member 140A is over molded onto the access member 140A. In this case, the material of the valve member 140A is formed in the openings 370 while the pillars 365 create corresponding openings 230 in the valve member 140A. In the example of FIG. 14A, the access member 135A includes four pillars 365 and four openings 370, but more or fewer pillars and openings may be included if desired.

FIG. 14B illustrates a bottom perspective view of the valve member 140A separated from the access member 135A. In the event that the valve member 140A is formed with an over molding process, it should be appreciated that views showing the valve member 140A separated from the access member 135A is for the purposes of illustration only, and does not necessarily suggest that valve member 140A is designed to be removable from the access member 135A after the over molding process is complete. In any event, FIG. 14B shows that the planar portion 215 includes the openings 230 and the groove 220. As further shown, a portion 235 of the planar portion 215 is located at a top of the groove 220 to enable needled extraction of the contents and to seal the contents at all other times.

FIG. 14C illustrates a bottom perspective view of the assembled access member 135A and valve member 140A (also referred to as a cap assembly with or without the inclusion of the housing 145) without showing bottom portions of the access member 135A and the valve member 140A to emphasize the existence of opening 240 through which the contents of the vial may be extracted via the port 315A. As shown, the planar portions 215 and 320A abut one another so that when fixed to the vial 105 by the housing 145 leakage of the contents at the rim of the vial 105 is prevented.

FIG. 14D illustrates a bottom perspective view of the assembled access member 135A and valve member 140A while showing bottom portions of the access member 135A and the valve member 140A. As shown, the groove 220 form fits to a back side of groove 360. As may be appreciated, the pillars 365 and openings 370 are not visible because the valve member 140A is formed in the openings 370 to surround the pillars 365.

FIG. 14E illustrates a top perspective view of the assembled access member 135A and valve member 140A. FIG. 14E illustrates how portions of the valve member 140A are exposed by the ports 350 and 355 to enable needled extraction. As shown, outer edges of the planar portion 320A and the planar portion 215 are substantially flush with one another.

FIG. 14F illustrates a see-through bottom perspective view of the assembled access member 135A and valve member 140A in order to show how the planar portion 215 of the valve member 140A covers the pillars 365 and openings 370 of the access member 135A.

Figure 15:
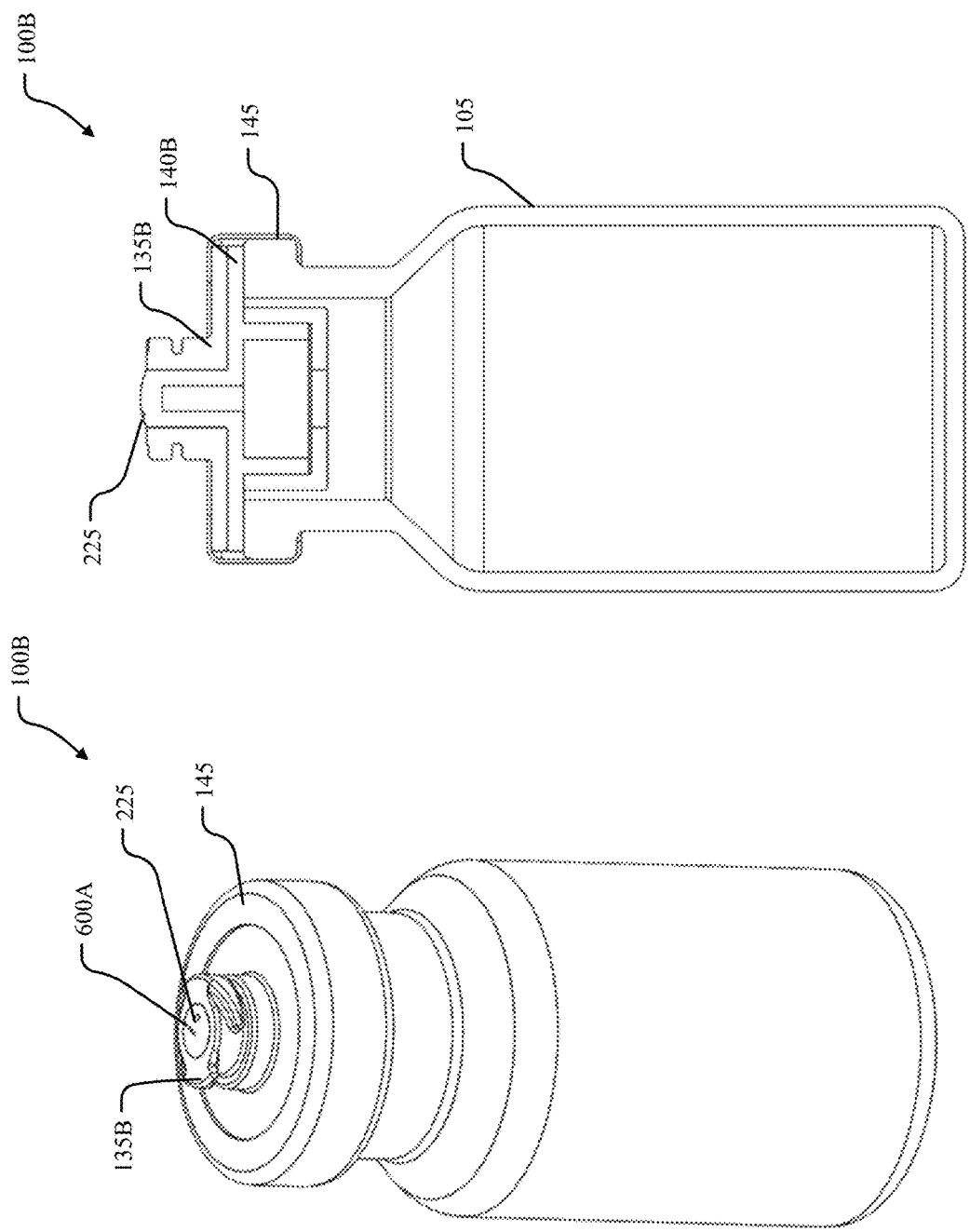
FIG. 15 illustrates a perspective view and a cross-sectional view of a vial assembly according to at least one example embodiment.

FIG. 15 illustrates a perspective view and a cross-sectional view of a vial assembly 100B according to at least one example embodiment. The vial assembly 100B includes a vial 105, an access member 135B, a valve member 140B, and a housing 145. FIG. 15 illustrates an example vial assembly having only the dimple 225 to assist with needled extraction of the contents from the vial 105. Thus, the access member 135B is different than the access member 135A in that the access member 135B does not include openings for ports 350 and 355 and does not include groove 360. The valve member 140B is different than the valve member 140A in that valve member 140B does not include groove 220. The access member 135B and valve member 140B may still include all other remaining structures (e.g., openings and pillars) shown for access member 135A and valve member 140A to enable the same over molding process described above.

Figure 16:
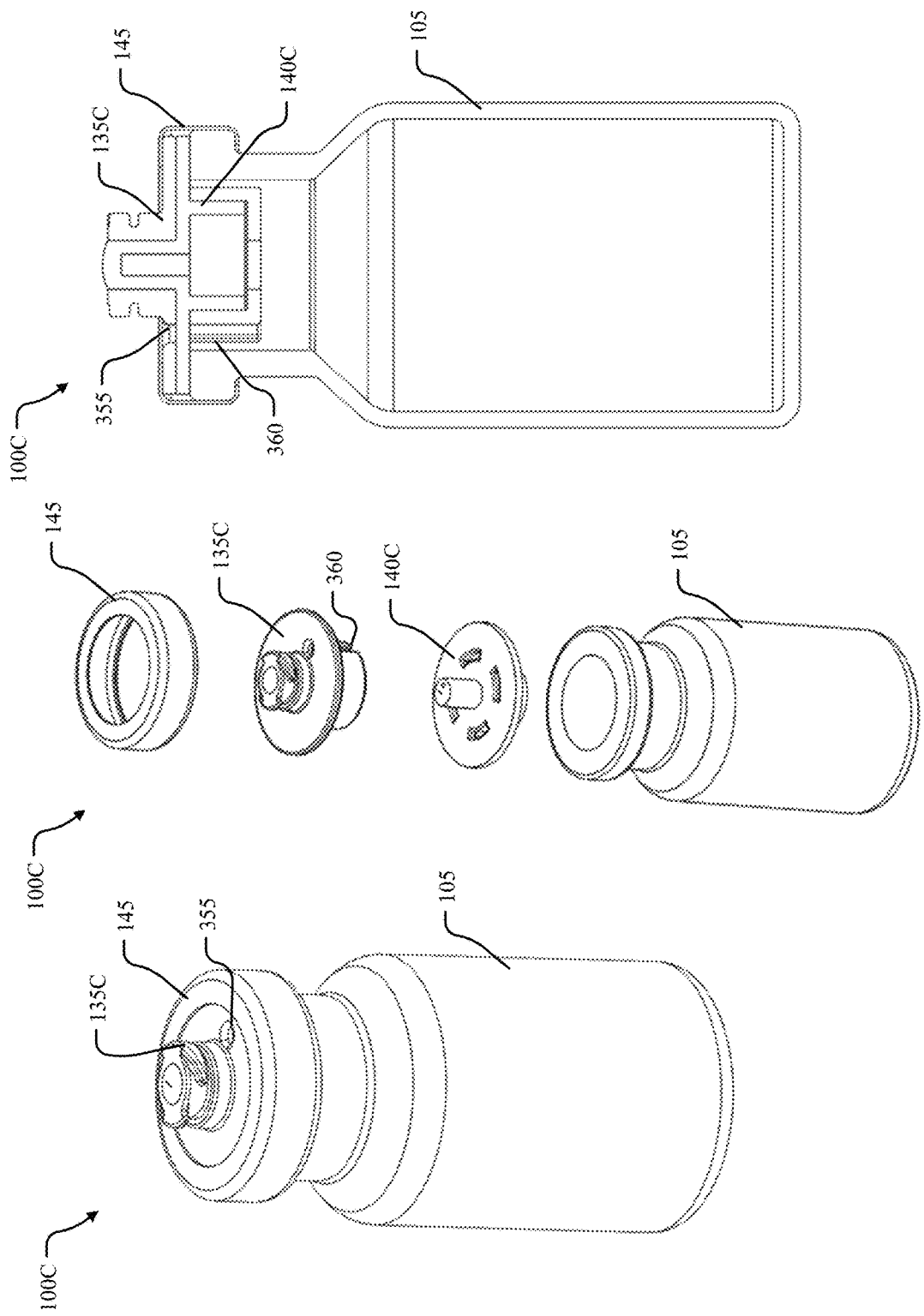
FIG. 16 illustrates a perspective view, an exploded view, and a cross-sectional view of a vial assembly according to at least one example embodiment.

FIG. 16 illustrates a perspective view, an exploded view, and a cross-sectional view of a vial assembly 100C according to at least one example embodiment. The vial assembly 100C includes a vial 105, an access member 135C, a valve member 140C, and housing 145. The vial assembly 100C includes a single port 355 for needled extraction of the contents in the same manner as that described above with reference to FIGS. 11-14. Accordingly, the access member 135C includes the groove 360 and the valve member 140C includes the groove 220. The access member 135C and valve member 140C may still include all other remaining structures (e.g., openings and pillars) shown for access member 135A and valve member 140A to enable the same over molding process described above.

Figure 17:
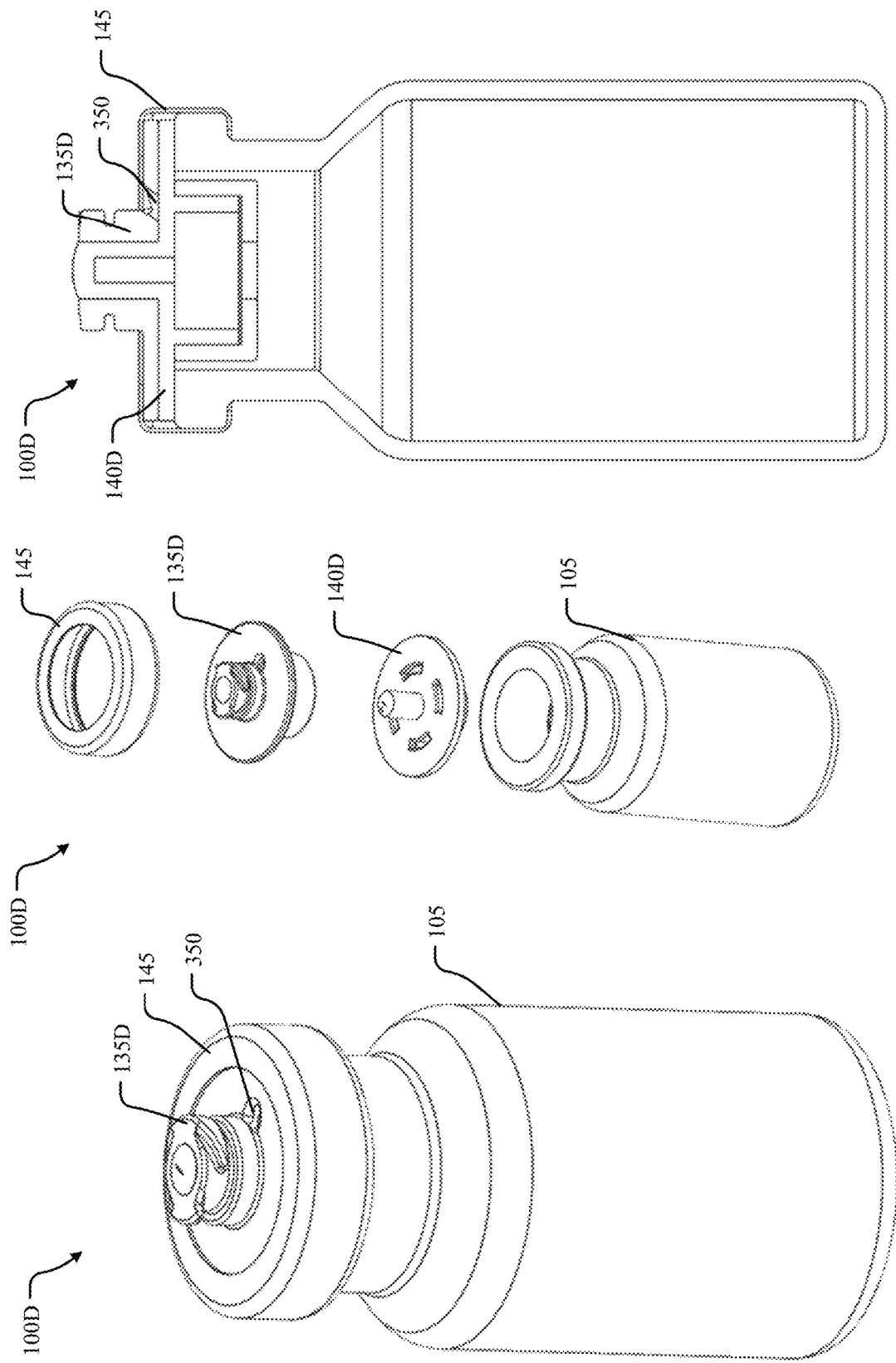
FIG. 17 illustrates a perspective view, an exploded view, and a cross-sectional view of a vial assembly according to at least one example embodiment.

FIG. 17 illustrates a perspective view, an exploded view, and a cross-sectional view of a vial assembly 100D according to at least one example embodiment. The vial assembly 100D includes a vial 105, an access member 135D, a valve member 140D, and housing 145. The vial assembly 100D includes a single port 350 for needled extraction of the contents in the same manner as that described above with reference to FIGS. 11-14. Accordingly, the grooves 360 and 220 in the access member 135D and the valve member 140D may be omitted. The access member 135D and valve member 140D may still include all other remaining structures (e.g., openings and pillars) shown for access member 135A and valve member 140A to enable the same over molding process described above.

FIGS. 11-17 illustrate examples where a valve member is over molded onto an access member. However, example embodiments are not limited thereto and other methods of forming the assembled valve member and access member are possible. For example, the valve member may be formed by a mold process to have the structure shown in FIG. 14B and then fitted onto the access member. In this case, the bottom of the access member may include protrusions (not shown) that correspond to the four openings 230 in the member, which allow the valve member to be slid onto the access member by inserting the protrusions into the openings 230 of the valve member.

In view of the above, it should be appreciated that example embodiments illustrated in FIGS. 1-10 may be modified to include the dimple, the straight needle port, the angled needled port, or any combination thereof if desired. In this case, the structure of the access member 135 in FIGS. 1-10 may be modified to look the same or similar to the access member of FIGS. 11-17 to include the port 350 and/or the port 355. For example, such port(s) of access member 135 in FIGS. 1-10 may be sealed by the valve member 140 so long as such port(s) is formed on the access member 135 in an area that overlaps the valve member 140. For a port 355, the groove 360 may be moved to an interior of the access member 135. For a port 350, the angled sidewalls of the access member may be angled to help guide a needle through the opening in the access member 140 and valve member 135. It should further be appreciated that the vial assemblies shown in FIGS. 11-17 are assembled in the same manner as in FIGS. 1-10 except that an over molding process may be performed to seat the valve member into the access member prior to crimping these elements to the vial with the housing.

It should be appreciated that example embodiments mitigate (or alternatively, eliminate) the disadvantages and risks of conventional devices that involve assembly of a needle to a syringe for insertion/extraction and administration of medicine from a vial. For example, a cap assembly according to example embodiments reduces the time required to assemble a device that can extract liquid from a vial since a needle does not have to be affixed to a separate syringe. Example embodiments also reduce (or alternatively eliminate) the risks associated with using a needle/syringe combination to extract and administer medicine to a patient. In addition, example embodiments provide for one or more backup ports for extraction using a needle in the event that needleless extraction is not possible or desirable.

For needleless administration of the fluid in the syringe, an IV line or drip can have a port that employs the same or similar concepts as those described above with respect to the cap assembly. For example, drip may have an access port that utilizes the same technology as the valve, the access member, the seal and the housing. Alternatively, the drip (or whatever device is intended to receive the now extracted liquid) may employ an assembly that has the same or similar technology as the valve and the access member, but have a different means of sealing/securing the access member/valve to the drip.

The foregoing description and figures show approximate dimensions (in inches) and example shapes and sizes of the valve, the seal, the access member, the housing, the syringe, the vial, etc. However, example embodiments are not limited to thereto, and the sizes and shapes of each element may vary according to design preferences (e.g., the size of the vial). In at least one example embodiment, the dimensions of the elements of a vial assembly may change so long as the relative dimensions between each element remain substantially the same. In addition, it should be understood that example embodiments are not limited to the types of connectors (e.g., male thread, female thread) disclosed herein. For example, other suitable connections (e.g., detent connections) may be employed if desired without departing from the spirit and scope of example embodiments.

The phrases "at least one", "one or more", "or", and "and/or" are open-ended expressions that are both conjunctive and disjunctive in operation. For example, each of the expressions "at least one of A, B and C", "at least one of A, B, or C", "one or more of A, B, and C", "one or more of A, B, or C", "A, B, and/or C", and "A, B, or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

Various aspects of the example embodiments are described herein with reference to drawings that are schematic illustrations of idealized configurations. It should be appreciated that while particular configurations and elements are described herein, example embodiments are not limited to the illustrative configurations and/or elements depicted and described herein. Specifically, it should be appreciated that elements of a particular type or function may be replaced with one or multiple other elements to achieve a similar function without departing from the scope of example embodiments.

The present disclosure, in various aspects, embodiments, and/or configurations, includes components, methods, processes, systems and/or apparatus substantially as depicted and described herein, including various aspects, embodiments, configurations embodiments, subcombinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and\or reducing cost of implementation.

The foregoing discussion has been presented for purposes of illustration and description. The foregoing is not intended to limit the disclosure to the form or forms disclosed herein. In the foregoing Detailed Description for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as an example embodiment of the disclosure.

At least one example embodiment includes a cap assembly including an access member including a first section and a second section, the first section including a connection portion that is attachable to an extraction device that extracts contents of a reservoir, the connection portion including a first opening, the second section including a second opening in fluid communication with the contents of the reservoir when the access member is secured to the reservoir. The cap assembly includes a valve member insertable into the access member and in fluid communication with the first opening and the second opening and such that the valve member i) seals the contents of the reservoir at the first opening when the connection portion is not attached the extraction device, and ii) provides access to the contents of the reservoir through the first opening when the connection portion is attached to the extraction device.

According to at least one example embodiment, the cap assembly includes a sealing member to seal an interface between the reservoir and the access member, and a housing that secures the access member and the sealing member to the reservoir.

According to at least one example embodiment, the housing is a bendable and hollow cylinder, and ends of the housing are bent toward a center of the cylinder to secure the access member and the sealing member to the reservoir.

According to at least one example embodiment, the housing is a metal.

According to at least one example embodiment, the valve member is a flexible material.

According to at least one example embodiment, the valve member is compressible and includes a top portion with a slit located in the first opening of the connection portion when the valve member is inserted into the access member.

According to at least one example embodiment, the slit, in an uncompressed state of the valve member, seals the contents of the reservoir at the first opening when the connection portion is not attached to the extraction device. The slit, in a compressed state of the valve member, provides the access to the contents of the reservoir when the connection portion is attached the extraction device.

According to at least one example embodiment, the first section and the second section are detachably connected.

According to at least one example embodiment, the connection portion protrudes from the access member and includes a male thread to engage with a female thread of the extraction device.

At least one example embodiment includes a vial assembly including a reservoir to hold contents, and a cap assembly fixable to the reservoir. The cap assembly includes an access member including a first section and a second section, the first section including a connection portion that is attachable to an extraction device that extracts the contents from the reservoir, the connection portion including a first opening, the second section including a second opening in fluid communication with the contents of the reservoir when the access member is secured to the reservoir. The cap assembly includes a valve member insertable into the access member and in fluid communication with the first opening and the second opening and such that the valve member i) seals the contents of the reservoir at the first opening when the connection portion is not attached the extraction device, and ii) provides access to the contents of the reservoir through the first opening when the connection portion is attached to the extraction device.

At least one example embodiment includes a package including a reservoir to hold contents, an extraction device to at least one of extract or insert the contents, a cap assembly fixable to the reservoir. The cap assembly includes an access member including a first section and a second section, the first section including a connection portion that is attachable to the extraction device that extracts contents of the reservoir, the connection portion including a first opening, the second section including a second opening in fluid communication with the contents of the reservoir when the access member is secured to the reservoir. The cap assembly includes a valve member insertable into the access member and in fluid communication with the first opening and the second opening and such that the valve member i) seals the contents of the reservoir at the first opening when the connection portion is not attached the extraction device, and ii) provides access to the contents of the reservoir through the first opening when the connection portion is attached to the extraction device.

At least one example embodiment includes a cap assembly including an access member configured for attachment to a reservoir. The access member includes a first port that enables needleless extraction of contents from the reservoir, and at least one second port that enables needled extraction of the contents from the reservoir. The cap assembly further includes a valve member positioned in or configured to be positioned in the access member to i) enable needleless extraction of the contents of the reservoir through the first port when the first port is attached to a needleless extraction device, ii) enable needled extraction of the contents through the at least one second port, and iii) seal the contents of the reservoir at the first port and at the at least one second port prior to and subsequent to the needleless or needled extraction.

According to at least one example embodiment, the access member includes a planar portion and a first portion that protrudes from a first side of the planar portion. The first portion includes the first port and is attachable to the needleless extraction device.

According to at least one example embodiment, the planar portion includes the at least one second port.

According to at least one example embodiment, the at least one second port comprises at least one opening in the planar portion.

According to at least one example embodiment, the at least one second port includes two ports.

According to at least one example embodiment, the access member includes a second portion that protrudes from a second side of the planar portion opposite the first side. The second portion includes a groove aligned with the at least one second port to guide a needle to the contents during needled extraction of the contents.

According to at least one example embodiment, the first portion includes threading that engages with corresponding threading on the needleless extraction device.

According to at least one example embodiment, the valve member includes a slit that is exposed by the first port of the access member when the valve member is positioned in the access member.

According to at least one example embodiment, the valve member is compressible, and the slit, in an uncompressed state of the valve member, seals the contents of the reservoir at the first port, and the slit, in a compressed state of the valve member, provides access to the contents of the reservoir for the needleless extraction device.

According to at least one example embodiment, the valve member includes a dimple arranged adjacent to the slit.

According to at least one example embodiment, an outermost diameter of the valve member is substantially equal to an outer most diameter of the access member.

According to at least one example embodiment, the cap assembly includes a housing configured to secure the access member and the valve member to the reservoir such that a portion of the valve member is between a rim of the reservoir and the access member.

According to at least one example embodiment, the housing is a bendable and hollow cylinder, and ends of the housing are bent toward a center of the hollow cylinder to secure the access member and the valve member to the reservoir.

At least one example embodiment is directed to a vial assembly including a reservoir to hold contents, and a cap assembly fixable to the reservoir. The cap assembly includes an access member configured for attachment to a reservoir. The access member includes a first port that enables needleless extraction of contents from the reservoir, and at least one second port that enables needled extraction of the contents from the reservoir. The cap assembly includes a valve member positioned in or configured to be positioned in the access member to i) enable needleless extraction of the contents of the reservoir through the first port when the first port is attached to a needleless extraction device, ii) enable needled extraction of the contents through the at least one second port, and iii) seal the contents of the reservoir at the first port and at the at least one second port prior to and subsequent to the needleless or needled extraction.

According to at least one example embodiment, the access member includes a planar portion and a first portion that protrudes from a first side of the planar portion. The first portion includes the first port and is attachable to the needleless extraction device.

According to at least one example embodiment, the planar portion includes the at least one second port.

According to at least one example embodiment, the at least one second port comprises at least one opening in the planar portion.

According to at least one example embodiment, the access member includes a second portion that protrudes from a second side of the planar portion opposite the first side, and the second portion includes a groove aligned with the at least one second port to guide a needle to the contents during needled extraction of the contents.

According to at least one example embodiment, the cap assembly includes a housing configured to secure the access member and the valve member to the reservoir such that a portion of the valve member is between a rim of the reservoir and the access member.

According to at least one example embodiment, a package includes a reservoir to hold contents an extraction device to extract the contents, and a cap assembly including an access member configured for attachment to a reservoir. The access member includes a first port that enables needleless extraction of contents from the reservoir, and at least one second port that enables needled extraction of the contents from the reservoir. The cap assembly includes a valve member positioned in or configured to be positioned in the access member to i) enable needleless extraction of the contents of the reservoir through the first port, ii) enable needled extraction of the contents through the at least one second port, and iii) seal the contents of the reservoir at the first port and at the at least one second port prior to and subsequent to the needleless or needled extraction. The cap assembly includes a housing configured to secure the access member and the valve member to the reservoir such that a portion of the valve member is between a rim of the reservoir and the access member.

What is claimed is:

1. A cap assembly, comprising:
an access member configured for attachment to a reservoir and including a first port; and
a valve member positioned in or configured to be positioned in the access member to i) enable needleless extraction of contents of the reservoir through the first port when the first port is attached to a needleless extraction device, and ii) seal the contents of the reservoir at the first port prior to and subsequent to the needleless extraction,
wherein the access member and the valve member are formed from different materials,
wherein the access member includes a planar portion,
wherein the valve member includes a planar portion, and
wherein an outermost diameter of the planar portion of the access member and an outermost diameter of the planar portion of the valve member are substantially the same.

2. The cap assembly of claim 1, wherein the access member further includes at least one second port that enables needled extraction of the contents from the reservoir, and wherein the at least one second port includes a first opening in the planar portion of the access member that exposes a first part of the planar portion of the valve member.

3. The cap assembly of claim 2, wherein the valve member seals the contents of the reservoir at the at least one second port prior to and subsequent to the needled extraction.

4. The cap assembly of claim 2, wherein the at least one second port includes a second opening in the planar portion of the access member that exposes a second part of the planar portion of the valve member.

5. The cap assembly of claim 4, wherein the second opening is defined by an angled sidewall of the access member.

6. The cap assembly of claim 5, wherein the angled sidewall is angled to guide a needle to the contents for needled extraction of the contents.

7. The cap assembly of claim 2, wherein the planar portion of the access member includes a first portion that protrudes from a first side of the planar portion of the access member, and wherein the first portion includes the first port and is attachable to the needleless extraction device.

8. The cap assembly of claim 7, wherein the access member includes a second portion that protrudes from a second side of the planar portion of the access member opposite the first side, and wherein the second portion includes a groove aligned with the first opening to guide a needle to the contents for needled extraction of the contents.

9. The cap assembly of claim 7, wherein the first portion of the planar portion of the access member includes threading that engages with corresponding threading on the needleless extraction device.

10. The cap assembly of claim 1, wherein the valve member includes a slit that is exposed by the first port of the access member when the valve member is positioned in the access member.

11. The cap assembly of claim 10, wherein the valve member is compressible, and wherein the slit, in an uncompressed state of the valve member, seals the contents of the reservoir at the first port, and wherein the slit, in a compressed state of the valve member, provides access to the contents of the reservoir for the needleless extraction device.

12. The cap assembly of claim 10, wherein the valve member includes a dimple arranged adjacent to the slit.

13. The cap assembly of claim 1, further comprising:
a housing configured to secure the access member and the valve member to the reservoir such that the planar portion of the valve member is between a rim of the reservoir and the planar portion of the access member.

14. A vial assembly, comprising:
a reservoir to hold contents; and
a cap assembly fixable to the reservoir, the cap assembly including:
an access member configured for attachment to the reservoir and including a first port; and
a valve member positioned in or configured to be positioned in the access member to i) enable needleless extraction of the contents of the reservoir through the first port when the first port is attached to a needleless extraction device, and ii) seal the contents of the reservoir at the first port prior to and subsequent to the needleless extraction,
wherein the access member and the valve member are formed from different materials,
wherein the access member includes a planar portion,
wherein the valve member includes a planar portion, and
wherein an outermost diameter of the planar portion of the access member and an outermost diameter of the planar portion of the valve member are substantially the same.

15. The vial assembly of claim 14, wherein the access member further includes at least one second port that enables needled extraction of the contents from the reservoir, and wherein the at least one second port includes a first opening in the planar portion of the access member that exposes a first part of the planar portion of the valve member.

16. The vial assembly of claim 15, wherein the valve member seals the contents of the reservoir at the at least one second port prior to and subsequent to the needled extraction.

17. The vial assembly of claim 15, wherein the at least one second port includes a second opening in the planar portion of the access member that exposes a second part of the planar portion of the valve member.

18. The vial assembly of claim 17, wherein the second opening is defined by an angled sidewall of the access member.

19. The vial assembly of claim 14, wherein the cap assembly further includes:
a housing configured to secure the access member and the valve member to the reservoir such that part of the planar portion of the valve member is between a rim of the reservoir and part of the planar portion of the access member.

20. A package, comprising:
a reservoir to hold contents;
an extraction device to extract the contents; and
a cap assembly including:
an access member configured for attachment to the reservoir and including a first port;
a valve member positioned in or configured to be positioned in the access member to i) enable needleless extraction of the contents of the reservoir through the first port, and ii) seal the contents of the reservoir at the first port prior to and subsequent to the needleless extraction,
wherein the access member and the valve member are formed from different materials,
wherein the access member includes a planar portion,
wherein the valve member includes a planar portion, and
wherein an outermost diameter of the planar portion of the access member and an outermost diameter of the planar portion of the valve member are substantially the same; and
a housing configured to secure the access member and the valve member to the reservoir such that part of the planar portion of the valve member is between a rim of the reservoir and part of the planar portion of the access member.

\* \* \* \* \*